United States Patent [19]

Hudson et al.

[11] Patent Number: 5,844,094
[45] Date of Patent: Dec. 1, 1998

[54] TARGET BINDING POLYPEPTIDE

[75] Inventors: Peter John Hudson; Maria Lah; Alex Andrew Kortt; Robert Alexander Irving; John Leslie Atwell; Robyn Louise Malby; Barbara Elaine Power; Peter Malcolm Colman, all of Melbourne, Australia

[73] Assignee: Commonwealth Scientific and Industrial Research Organization, Campbell, Australia

[21] Appl. No.: 403,853

[22] PCT Filed: Sep. 24, 1993

[86] PCT No.: PCT/AU93/00491

§ 371 Date: May 30, 1995

§ 102(e) Date: May 30, 1995

[87] PCT Pub. No.: WO94/07921

PCT Pub. Date: Apr. 14, 1994

[30] Foreign Application Priority Data

Sep. 25, 1992 [AU] Australia ................................ PL4973

[51] Int. Cl.$^6$ .............................. C12P 21/08; C07K 16/00
[52] U.S. Cl. ..................................... 530/387.3; 536/23.53; 435/328
[58] Field of Search ............................ 530/387.3, 388.3, 530/417; 536/23.53; 435/328

[56] References Cited

FOREIGN PATENT DOCUMENTS

| | | |
|---|---|---|
| B-12992/92 | 3/1991 | Australia . |
| 0 239 400 | 9/1987 | European Pat. Off. . |
| 92105380 | 3/1992 | European Pat. Off. . |
| WO 85/02121 | 5/1985 | WIPO . |
| WO A 88 01649 | 3/1988 | WIPO . |
| WO 90/00614 | 1/1990 | WIPO . |
| 9002809 | 3/1990 | WIPO . |
| PCT/US09965 | 11/1991 | WIPO . |
| WO 91/16927 | 11/1991 | WIPO . |
| 9201047 | 1/1992 | WIPO . |
| WO A 92 01787 | 2/1992 | WIPO . |
| WO 92/10670 | 6/1992 | WIPO . |
| WO 93/1161 | 6/1993 | WIPO . |

OTHER PUBLICATIONS

Bird et al., Single chain antiody variable regions, *TIBTECH*, vol. 9, Apr., 1991, pp. 132–137.
Bird et al., Single–Chain Antigen–Binding Proteins, *Science*, vol. 242 Oct. 21, 1988, pp. 423–426.
Huston et al., Protein engineering of antibody binding sites: Recovery of specific activity in an anti–digoxin single–chain Fv analogue producted in *Escherichia coli*. *Proc. Natl. Acad. Sci. USA* vol. 85, pp. 5879–5883.
Colcher et al. In vivo Tumor Targeting of a Recombinant Single–Chain Antigen–Binding Protein, *Journal of the National Cancer Institute*, vol. 82, No. 14, Jul. 18, 1990.
Sharon, "Structural correlates of high antibody affinity: Three engineered amino acid substitutions . . . ", *Proc. Natl. Acad. Sci. USA* 87: 4814–4817 (1990).
Lehninger, "Principles of Biochemistry", Worth Publishers, Inc., New York, 1982, Chapter 30, pp. 926–933.
Erlich, "PCR Technology, Principles and Applications for DNA Amplification", Stockton Press, New York, 1989, Part 1, pp. 1–5.
Callow, "Measurement of Antibodies to Influenza Virus Neuraminidase by an Enzyme–Linked Immunosorbent Assay", Infection and Immunity, vol. 41(2) Aug. 1983, pp. 650–656.
Sorvillo et al., "Preparation and Characterization of Monoclonal Antibodies Specific for Human Transforming Growth Factor Alpha", Chemical Abstracts, vol. 113, No. 1, 1990, abstract No. 4322f.
Callow, K.A. 1983 Infection & Immunity, 41:650–656.
Schaaper, R.M. 1988 PMAS, USA 85:8126–8130.
Pack, P. et al. Biochemistry 31(6):4570–4584, 1992.
McCartney et al. J. Protein Chemistry 10(6):669–683, 1991.
George, AJT et al. J. Cell Biochem. Suppl. 15 (Part E), p. 127, 1991.
Whitlow, H. et al. Methods 2(2):97–105, 1991.

*Primary Examiner*—Toni R. Scheiner
*Attorney, Agent, or Firm*—Foley & Lardner

[57] ABSTRACT

A target-binding polypeptide having (a) a stable core polypeptide region (SCR); and (b) at least one target-binding region (TBR), in which the target-binding region(s) are covalently attached to the SCR and which have optionally been subjected to a maturation step in order to modify the specificity, the affinity or the avidity of binding to the target. The polypeptides may self associate to form stable dimers, aggregates or arrays. The polypeptides of the invention have utility in the diagnostic, therapeutic, predictive or preventative fields of the pharmaceutical and health care industries, as well as more general application in the detection and assay of chemical entities.

20 Claims, 19 Drawing Sheets

DELETION LINKER CONSTRUCTS

| Construct | Complementary Oligonucleotide Pair |
|---|---|
| ((Gly4)Ser)3 | 5' GTC ACC GTC TCC (GGT GGT GGT GGT TCG)3 GAT ATC GAG CT 3'<br>3'          G CAG AGG (CCA CCA CCA CCA AGC)3 CTA TAG C     5' |
| ((Gly4)Ser)2 | 5' GTC ACC GTC TCC (GGT GGT GGT GGT TCG)2 GAT ATC CAG CT 3'<br>3'          G CAG AGG (CCA CCA CCA CCA AGC)2 CTA TAG C     5' |
| (Gly4)Ser | 5' GTC ACC GTC TCC GGT GGT GGT GGT TCG GAT ATC GAG CT 3'<br>3'          G CAG AGG CCA CCA CCA CCA AGC CTA TAG C     5' |
| – | 5' GTC ACC GTC TCC GAT ATC GAG CT 3'<br>3'          G CAG AGG CTA TAG C     5' |

-13.VL  5' GGG ACC ACG GTC ACC GTC TCC TCA GCC TCT CTG GGA GAC AGA GTC ACC

5' GTC GAC GAA TTC TTA TTA TTT ATC GTC ATC ATC TTT GTA GTC 3'

FIGURE 6

DELETION LINKER CONSTRUCTS

| Linker Unit | Observed Forms | Activity |
|---|---|---|
| ((Gly$_4$)Ser)$_3$ | Monomers & dimers | ++ |
| ((Gly$_4$)Ser)$_2$ | Dimers | ++ |
| (Gly$_4$)Ser | Dimers | ++ |
| - | Multimers | + |
| -13.VL△ | Multimers | |

FIGURE 8

Formation of Dimeric scFvs
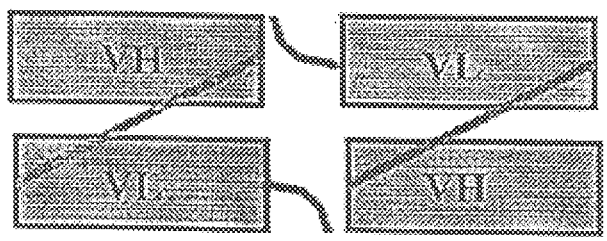
or
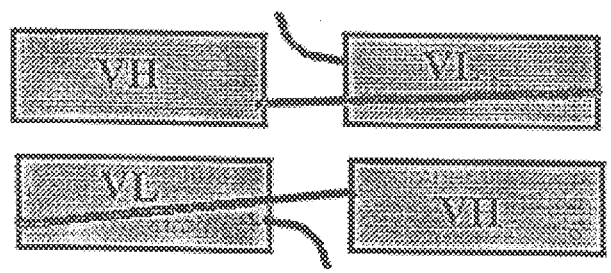
FIGURE 17

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

ACGTAGGTCA CCGTCGCCTC CGACATCGTC ATGTCACAGT CTCCATCCTC C          51

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TTTATAATCT GCGGCCGCCC GATTAATTTC          30

( 2 ) INFORMATION FOR SEQ ID NO:3:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

Phe Thr Ala Ser Thr Gly Asp Val Pro Asp Arg Phe Ser Gly Ser Gly
 1               5                  10                  15

Ser Gly Thr Asp Phe Thr Leu Arg Ile Ser Ser Leu Gln Ala Glu Asp
                20                  25                  30

Val Ala Val Tyr Tyr Cys Gln Gln Ala Ser Val Phe Pro
            35                  40                  45

( 2 ) INFORMATION FOR SEQ ID NO:4:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

Cys Ile Tyr Trp Asn Pro Asp Ser Pro Asp Arg Phe Ser Gly Ser Gly
 1               5                  10                  15

Ser Gly Thr Asp Phe Thr Leu Arg Ile Ser Leu Gln Ala Glu Asp Val
                20                  25                  30

Ala Val Tyr Tyr Cys Gln Gln Ala Ser Val Phe Pro
            35                  40

( 2 ) INFORMATION FOR SEQ ID NO:5:

( i ) SEQUENCE CHARACTERISTICS:
  ( A ) LENGTH: 43 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:5:

```
CCTTGCCTGC AGGTCGACCT ATGGACAGGT GCAGCTGCAG CAG                    43
```

( 2 ) INFORMATION FOR SEQ ID NO:6:

( i ) SEQUENCE CHARACTERISTICS:
  ( A ) LENGTH: 69 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:6:

```
TTACCATGGT TACTTGACCT TAATCAGCAG GACAAATGAA ATAAATTTAT CATCATCATC   60
TTTATAATC                                                          69
```

( 2 ) INFORMATION FOR SEQ ID NO:7:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:7:

```
CAGGTCGACT CTAGAGTATG GGAGGTGAGG CTTCTCGAG                         39
```

( 2 ) INFORMATION FOR SEQ ID NO:8:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:8:

```
AAATTTATAA TTATTTATCA TCATCATCTT TATAATC                           37
```

( 2 ) INFORMATION FOR SEQ ID NO:9:

( i ) SEQUENCE CHARACTERISTICS:
  ( A ) LENGTH: 849 base pairs
  ( B ) TYPE: nucleic acid
  ( C ) STRANDEDNESS: single
  ( D ) TOPOLOGY: linear ( i x ) FEATURE:
  ( A ) NAME/KEY: mat_peptide
  ( B ) LOCATION: 1..840

( i x ) FEATURE:
  ( A ) NAME/KEY: CDS
  ( B ) LOCATION: 1..840

( x i ) SEQUENCE DESCRIPTION: SEQ ID NO:9:

```
ATG AAA TAC CTA TTG CCT ACG GCA GCC GCT GGA TTG TTA TTA CTC GCT    48
Met Lys Tyr Leu Leu Pro Thr Ala Ala Ala Gly Leu Leu Leu Leu Ala
 1               5                  10                  15

GCC CAA CCA GCG ATG GCC AAG CCA CAG GCA CCC GAA CTC CGA ATC TTT    96
Ala Gln Pro Ala Met Ala Lys Pro Gln Ala Pro Glu Leu Arg Ile Phe
```

|  |  |  |  |  |  |  |  |  |  |  |  |  |  |  |  |
|---|---|---|---|---|---|---|---|---|---|---|---|---|---|---|---|
|  |  | 20 |  |  |  |  | 25 |  |  |  |  | 30 |  |  |  |
| CCA | AAG | AAA | ATG | GAC | GCC | GAA | CTT | GGT | CAG | AAG | GTG | GAC | CTG | GTA | TGT | 144 |
| Pro | Lys | Lys 35 | Met | Asp | Ala | Glu | Leu 40 | Gly | Gln | Lys | Val | Asp 45 | Leu | Val | Cys |  |
| GAA | GTG | TTG | GGG | TCC | GTT | TCG | CAA | GGA | TGC | TCT | TGG | CTC | TTC | CAG | AAC | 192 |
| Glu | Val 50 | Leu | Gly | Ser | Val | Ser 55 | Gln | Gly | Cys | Ser | Trp 60 | Leu | Phe | Gln | Asn |  |
| TCC | AGC | TCC | AAA | CTC | CCC | CAG | CCC | ACC | TTC | GTT | GTC | TAT | ATG | GCT | TCA | 240 |
| Ser 65 | Ser | Ser | Lys | Leu | Pro 70 | Gln | Pro | Thr | Phe | Val 75 | Val | Tyr | Met | Ala | Ser 80 |  |
| TCC | CAC | AAC | AAG | ATA | ACG | TGG | GAC | GAG | AAG | CTG | AAT | TCG | TCG | AAA | CTG | 288 |
| Ser | His | Asn | Lys | Ile 85 | Thr | Trp | Asp | Glu | Lys 90 | Leu | Asn | Ser | Ser | Lys 95 | Leu |  |
| TTT | TCT | GCC | ATG | AGG | GAC | ACG | AAT | AAT | AAG | TAC | GTT | CTC | ACC | CTG | AAC | 336 |
| Phe | Ser | Ala | Met 100 | Arg | Asp | Thr | Asn | Asn 105 | Lys | Tyr | Val | Leu | Thr 110 | Leu | Asn |  |
| AAG | TTC | AGC | AAG | GAA | AAC | GAA | GGC | TAC | TAT | TTC | TGC | TCA | GTC | ATC | AGC | 384 |
| Lys | Phe | Ser 115 | Lys | Glu | Asn | Glu | Gly | Tyr 120 | Tyr | Phe | Cys | Ser | Val 125 | Ile | Ser |  |
| AAC | TCG | GTG | ATG | TAC | TTC | AGT | TCT | GTC | GTG | CCA | GTC | CTT | CAG | GGT | GGC | 432 |
| Asn | Ser | Val 130 | Met | Tyr | Phe | Ser | Ser 135 | Val | Val | Pro | Val | Leu 140 | Gln | Gly | Gly |  |
| GGA | GGC | TCA | GGC | GGT | GGT | GGA | TCA | GGT | GGC | GGC | GGA | TCT | CTC | ATT | CAG | 480 |
| Gly 145 | Gly | Ser | Gly | Gly | Gly 150 | Gly | Ser | Gly | Gly | Gly 155 | Gly | Ser | Leu | Ile | Gln 160 |  |
| ACC | CCT | TCG | TCC | CTG | CTG | GTT | CAA | ACC | AAC | CAT | ACG | GCA | AAG | ATG | TCC | 528 |
| Thr | Pro | Ser | Ser | Leu 165 | Leu | Val | Gln | Thr | Asn 170 | His | Thr | Ala | Lys | Met 175 | Ser |  |
| TGT | GAG | GTT | AAA | AGC | ATC | TCT | AAG | TTA | ACA | AGC | ATC | TAC | TGG | CTG | CGG | 576 |
| Cys | Glu | Val | Lys 180 | Ser | Ile | Ser | Lys | Leu 185 | Thr | Ser | Ile | Tyr | Trp 190 | Leu | Arg |  |
| GAG | CGC | CAG | GAC | CCC | AAG | GAC | AAG | TAC | TTT | GAG | TTC | CTG | GCC | TCC | TGG | 624 |
| Glu | Arg | Gln 195 | Asp | Pro | Lys | Asp | Lys 200 | Tyr | Phe | Glu | Phe | Leu 205 | Ala | Ser | Trp |  |
| AGT | TCT | TCC | AAA | GGA | GTT | TTG | TAT | GGT | GAA | AGT | GTG | GAC | AAG | AAA | AGA | 672 |
| Ser | Ser | Ser 210 | Lys | Gly | Val | Leu | Tyr 215 | Gly | Glu | Ser | Val | Asp 220 | Lys | Lys | Arg |  |
| AAT | ATA | ATT | CTT | GAG | TCT | TCA | GAC | TCA | AGA | CGG | CCC | TTT | CTC | AGT | ATC | 720 |
| Asn 225 | Ile | Ile | Leu | Glu | Ser 230 | Ser | Asp | Ser | Arg | Arg 235 | Pro | Phe | Leu | Ser | Ile 240 |  |
| ATG | AAT | GTG | AAG | CCA | GAG | GAC | AGT | GAC | TTC | TAC | TTC | TGC | GCG | ACG | GTT | 768 |
| Met | Asn | Val | Lys | Pro 245 | Glu | Asp | Ser | Asp | Phe 250 | Tyr | Phe | Cys | Ala | Thr 255 | Val |  |
| GGG | AGC | CCC | AAG | ATG | GTC | TTT | GGG | ACA | GGG | ACG | AAG | CTG | ACT | GTG | GTT | 816 |
| Gly | Ser | Pro | Lys | Met 260 | Val | Phe | Gly | Thr | Gly 265 | Thr | Lys | Leu | Thr 270 | Val | Val |  |
| GAT | TAC | AAG | GAC | GAC | GAT | GAC | AAG | TAGTCGACA |  |  |  |  |  |  |  | 849 |
| Asp | Tyr | Lys 275 | Asp | Asp | Asp | Asp | Lys 280 |  |  |  |  |  |  |  |  |  |

( 2 ) INFORMATION FOR SEQ ID NO:10:

( i ) SEQUENCE CHARACTERISTICS:
        ( A ) LENGTH: 280 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | Lys | Tyr | Leu | Leu | Pro | Thr | Ala | Ala | Ala | Gly | Leu | Leu | Leu | Leu | Ala |
|---|---|---|---|---|---|---|---|---|---|---|---|---|---|---|---|
| 1 |  |  |  | 5 |  |  |  |  | 10 |  |  |  |  | 15 |  |

| | | | | | | | | | | | | | | |
|---|---|---|---|---|---|---|---|---|---|---|---|---|---|---|
| Ala | Gln | Pro | Ala<br>20 | Met | Ala | Lys | Pro | Gln<br>25 | Ala | Pro | Glu | Leu | Arg<br>30 | Ile | Phe |
| Pro | Lys | Met<br>35 | Asp | Ala | Glu | Leu<br>40 | Gly | Gln | Lys | Val | Asp<br>45 | Leu | Val | Cys |
| Glu | Val<br>50 | Leu | Gly | Ser | Val | Ser<br>55 | Gln | Gly | Cys | Ser | Trp<br>60 | Leu | Phe | Gln | Asn |
| Ser<br>65 | Ser | Ser | Lys | Leu | Pro<br>70 | Gln | Pro | Thr | Phe | Val<br>75 | Val | Tyr | Met | Ala | Ser<br>80 |
| Ser | His | Asn | Lys | Ile<br>85 | Thr | Trp | Asp | Glu | Lys<br>90 | Leu | Asn | Ser | Ser | Lys<br>95 | Leu |
| Phe | Ser | Ala | Met<br>100 | Arg | Asp | Thr | Asn | Asn<br>105 | Lys | Tyr | Val | Leu | Thr<br>110 | Leu | Asn |
| Lys | Phe | Ser<br>115 | Lys | Glu | Asn | Glu | Gly<br>120 | Tyr | Tyr | Phe | Cys | Ser<br>125 | Val | Ile | Ser |
| Asn | Ser<br>130 | Val | Met | Tyr | Phe | Ser<br>135 | Ser | Val | Val | Pro | Val<br>140 | Leu | Gln | Gly | Gly |
| Gly<br>145 | Gly | Ser | Gly | Gly | Gly<br>150 | Gly | Ser | Gly | Gly | Gly<br>155 | Gly | Ser | Leu | Ile | Gln<br>160 |
| Thr | Pro | Ser | Ser | Leu<br>165 | Leu | Val | Gln | Thr | Asn<br>170 | His | Thr | Ala | Lys | Met<br>175 | Ser |
| Cys | Glu | Val | Lys<br>180 | Ser | Ile | Ser | Lys | Leu<br>185 | Thr | Ser | Ile | Tyr | Trp<br>190 | Leu | Arg |
| Glu | Arg | Gln<br>195 | Asp | Pro | Lys | Asp | Lys<br>200 | Tyr | Phe | Glu | Phe | Leu<br>205 | Ala | Ser | Trp |
| Ser | Ser<br>210 | Ser | Lys | Gly | Val | Leu<br>215 | Tyr | Gly | Glu | Ser | Val<br>220 | Asp | Lys | Lys | Arg |
| Asn<br>225 | Ile | Ile | Leu | Glu | Ser<br>230 | Ser | Asp | Ser | Arg | Arg<br>235 | Pro | Phe | Leu | Ser | Ile<br>240 |
| Met | Asn | Val | Lys | Pro<br>245 | Glu | Asp | Ser | Asp | Phe<br>250 | Tyr | Phe | Cys | Ala | Thr<br>255 | Val |
| Gly | Ser | Pro | Lys | Met<br>260 | Val | Phe | Gly | Thr<br>265 | Gly | Thr | Lys | Leu | Thr<br>270 | Val | Val |
| Asp | Tyr | Lys<br>275 | Asp | Asp | Asp | Asp | Lys<br>280 | | | | | | | | |

(2) INFORMATION FOR SEQ ID NO:11:

(i) SEQUENCE CHARACTERISTICS:
        (A) LENGTH: 822 base pairs
        (B) TYPE: nucleic acid
        (C) STRANDEDNESS: single
        (D) TOPOLOGY: linear (ix) FEATURE:
        (A) NAME/KEY: mat_peptide
        (B) LOCATION: 1..819

(ix) FEATURE:
        (A) NAME/KEY: CDS
        (B) LOCATION: 1..819

(xi) SEQUENCE DESCRIPTION: SEQ ID NO:11:

| | | | | | | | | | | | | | | | | |
|---|---|---|---|---|---|---|---|---|---|---|---|---|---|---|---|---|
| ATG | AAA | TAC | CTA | TTG | CCT | ACG | GCA | GCC | GCT | GGA | TTG | TTA | TTA | CTC | GCT | 48 |
| Met<br>1 | Lys | Tyr | Leu | Leu<br>5 | Pro | Thr | Ala | Ala | Ala<br>10 | Gly | Leu | Leu | Leu | Leu<br>15 | Ala | |
| GCC | CAA | CCA | GCG | ATG | GCC | AGC | CAG | TTC | CGG | GTG | TCG | CCG | CTG | GAT | CGG | 96 |
| Ala | Gln | Pro | Ala<br>20 | Met | Ala | Ser | Gln | Phe<br>25 | Arg | Val | Ser | Pro | Leu<br>30 | Asp | Arg | |
| ACC | TGG | AAC | CTG | GGC | GAG | ACA | GTG | GAG | CTG | AAG | TGC | CAG | GTG | CTG | CTG | 144 |

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Thr | Trp | Asn | Leu | Gly | Glu | Thr | Val | Glu | Leu | Lys | Cys | Gln | Val | Leu | Leu |     |
|     |     | 35  |     |     |     | 40  |     |     |     |     | 45  |     |     |     |     |     |
| TCC | AAC | CCG | ACG | TCG | GGC | TGC | TCG | TGG | CTC | TTC | CAG | CCG | CGC | GGC | GCC | 192 |
| Ser | Asn | Pro | Thr | Ser | Gly | Cys | Ser | Trp | Leu | Phe | Gln | Pro | Arg | Gly | Ala |     |
|     | 50  |     |     |     | 55  |     |     |     |     | 60  |     |     |     |     |     |     |
| GCC | GCC | AGT | CCC | ACC | TTC | CTC | CTA | TAC | CTC | TCC | CAA | AAC | AAG | CCC | AAG | 240 |
| Ala | Ala | Ser | Pro | Thr | Phe | Leu | Leu | Tyr | Leu | Ser | Gln | Asn | Lys | Pro | Lys |     |
| 65  |     |     |     | 70  |     |     |     |     | 75  |     |     |     |     | 80  |     |     |
| GCG | GCC | GAG | GGG | CTG | GAC | ACC | CAG | CGG | TTC | TCG | GGC | AAG | AGG | TTG | GGG | 288 |
| Ala | Ala | Glu | Gly | Leu | Asp | Thr | Gln | Arg | Phe | Ser | Gly | Lys | Arg | Leu | Gly |     |
|     |     |     |     | 85  |     |     |     |     | 90  |     |     |     |     | 95  |     |     |
| GAC | ACC | TTC | GTC | CTC | ACC | CTG | AGC | GAC | TTC | CGC | CGA | GAG | AAC | GAG | GGC | 336 |
| Asp | Thr | Phe | Val | Leu | Thr | Leu | Ser | Asp | Phe | Arg | Arg | Glu | Asn | Glu | Gly |     |
|     |     |     | 100 |     |     |     | 105 |     |     |     |     | 110 |     |     |     |     |
| TAC | TAT | TTC | TGC | TCG | GCC | CTG | AGC | AAC | TCC | ATC | ATG | TAC | TTC | AGC | CAC | 384 |
| Tyr | Tyr | Phe | Cys | Ser | Ala | Leu | Ser | Asn | Ser | Ile | Met | Tyr | Phe | Ser | His |     |
|     |     | 115 |     |     |     |     | 120 |     |     |     |     | 125 |     |     |     |     |
| TTC | GTG | CCG | GTC | TTC | CTG | CCA | GCG | GGC | GGC | CGC | GGT | TCA | GGT | GGA | GGT | 432 |
| Phe | Val | Pro | Val | Phe | Leu | Pro | Ala | Gly | Gly | Arg | Gly | Ser | Gly | Gly | Gly |     |
|     | 130 |     |     |     |     | 135 |     |     |     |     | 140 |     |     |     |     |     |
| GGA | TCC | GGA | GGC | GGT | GGA | TCT | CTC | CAG | CAG | ACC | CCT | GCA | TAC | ATA | AAG | 480 |
| Gly | Ser | Gly | Gly | Gly | Gly | Ser | Leu | Gln | Gln | Thr | Pro | Ala | Tyr | Ile | Lys |     |
| 145 |     |     |     |     | 150 |     |     |     |     | 155 |     |     |     |     | 160 |     |
| GTG | CAA | ACC | AAC | AAG | ATG | GTG | ATG | CTG | TCC | TGC | GAG | GCT | AAA | ATC | TCC | 528 |
| Val | Gln | Thr | Asn | Lys | Met | Val | Met | Leu | Ser | Cys | Glu | Ala | Lys | Ile | Ser |     |
|     |     |     |     | 165 |     |     |     |     | 170 |     |     |     |     | 175 |     |     |
| CTC | AGT | AAC | ATG | CGC | ATC | TAC | TGG | CTG | AGA | CAG | CGC | CAG | GCA | CCG | AGC | 576 |
| Leu | Ser | Asn | Met | Arg | Ile | Tyr | Trp | Leu | Arg | Gln | Arg | Gln | Ala | Pro | Ser |     |
|     |     |     | 180 |     |     |     |     | 185 |     |     |     |     | 190 |     |     |     |
| AGT | GAC | AGT | CAC | CAC | GAG | TTC | CTG | GCC | CTC | TGG | GAT | TCC | GCA | AAA | GGG | 624 |
| Ser | Asp | Ser | His | His | Glu | Phe | Leu | Ala | Leu | Trp | Asp | Ser | Ala | Lys | Gly |     |
|     |     | 195 |     |     |     |     | 200 |     |     |     |     | 205 |     |     |     |     |
| ACT | ATC | CAC | GGT | GAA | GAG | GTG | GAA | CAG | GAG | AAG | ATA | GCT | GTG | TTT | CGG | 672 |
| Thr | Ile | His | Gly | Glu | Glu | Val | Glu | Gln | Glu | Lys | Ile | Ala | Val | Phe | Arg |     |
|     | 210 |     |     |     |     | 215 |     |     |     |     | 220 |     |     |     |     |     |
| GAT | GCA | AGC | CGG | TTC | ATT | CTC | AAT | CTC | ACA | AGC | GTG | AAG | CCG | GAA | GAC | 720 |
| Asp | Ala | Ser | Arg | Phe | Ile | Leu | Asn | Leu | Thr | Ser | Val | Lys | Pro | Glu | Asp |     |
| 225 |     |     |     |     | 230 |     |     |     |     | 235 |     |     |     |     | 240 |     |
| AGT | GGC | ATC | TAC | TTC | TGC | ATG | ATC | GTC | GGG | AGC | CCC | GAG | CTG | ACC | TTC | 768 |
| Ser | Gly | Ile | Tyr | Phe | Cys | Met | Ile | Val | Gly | Ser | Pro | Glu | Leu | Thr | Phe |     |
|     |     |     |     | 245 |     |     |     |     | 250 |     |     |     |     | 255 |     |     |
| GGG | AAG | GGA | ACT | CAG | CTG | AGT | GTG | GTT | GAT | TAC | AAG | GAC | GAC | GAT | GAC | 816 |
| Gly | Lys | Gly | Thr | Gln | Leu | Ser | Val | Val | Asp | Tyr | Lys | Asp | Asp | Asp | Asp |     |
|     |     |     | 260 |     |     |     |     | 265 |     |     |     |     | 270 |     |     |     |
| AAG | TAG |     |     |     |     |     |     |     |     |     |     |     |     |     |     | 822 |
| Lys |     |     |     |     |     |     |     |     |     |     |     |     |     |     |     |     |

( 2 ) INFORMATION FOR SEQ ID NO:12:

( i ) SEQUENCE CHARACTERISTICS:
  ( A ) LENGTH: 273 amino acids
  ( B ) TYPE: amino acid
  ( D ) TOPOLOGY: linear ( i i ) MOLECULE TYPE: protein ( x i ) SEQUENCE DESCRIPTION: SEQ ID NO:12:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Lys | Tyr | Leu | Leu | Pro | Thr | Ala | Ala | Ala | Gly | Leu | Leu | Leu | Leu | Ala |
| 1   |     |     |     | 5   |     |     |     |     | 10  |     |     |     |     | 15  |     |
| Ala | Gln | Pro | Ala | Met | Ala | Ser | Gln | Phe | Arg | Val | Ser | Pro | Leu | Asp | Arg |
|     |     |     | 20  |     |     |     |     | 25  |     |     |     |     | 30  |     |     |

```
Thr  Trp  Asn  Leu  Gly  Glu  Thr  Val  Glu  Leu  Lys  Cys  Gln  Val  Leu  Leu
          35                  40                  45

Ser  Asn  Pro  Thr  Ser  Gly  Cys  Ser  Trp  Leu  Phe  Gln  Pro  Arg  Gly  Ala
     50                  55                  60

Ala  Ala  Ser  Pro  Thr  Phe  Leu  Leu  Tyr  Leu  Ser  Gln  Asn  Lys  Pro  Lys
65                       70                  75                            80

Ala  Ala  Glu  Gly  Leu  Asp  Thr  Gln  Arg  Phe  Ser  Gly  Lys  Arg  Leu  Gly
                    85                  90                       95

Asp  Thr  Phe  Val  Leu  Thr  Leu  Ser  Asp  Phe  Arg  Arg  Glu  Asn  Glu  Gly
               100                 105                           110

Tyr  Tyr  Phe  Cys  Ser  Ala  Leu  Ser  Asn  Ser  Ile  Met  Tyr  Phe  Ser  His
          115                      120                      125

Phe  Val  Pro  Val  Phe  Leu  Pro  Ala  Gly  Arg  Gly  Ser  Gly  Gly  Gly
     130                      135                      140

Gly  Ser  Gly  Gly  Gly  Gly  Ser  Leu  Gln  Gln  Thr  Pro  Ala  Tyr  Ile  Lys
145                      150                      155                      160

Val  Gln  Thr  Asn  Lys  Met  Val  Met  Leu  Ser  Cys  Glu  Ala  Lys  Ile  Ser
               165                      170                      175

Leu  Ser  Asn  Met  Arg  Ile  Tyr  Trp  Leu  Arg  Gln  Arg  Gln  Ala  Pro  Ser
               180                      185                      190

Ser  Asp  Ser  His  His  Glu  Phe  Leu  Ala  Leu  Trp  Asp  Ser  Ala  Lys  Gly
          195                      200                      205

Thr  Ile  His  Gly  Glu  Glu  Val  Glu  Gln  Glu  Lys  Ile  Ala  Val  Phe  Arg
     210                      215                      220

Asp  Ala  Ser  Arg  Phe  Ile  Leu  Asn  Leu  Thr  Ser  Val  Lys  Pro  Glu  Asp
225                      230                      235                      240

Ser  Gly  Ile  Tyr  Phe  Cys  Met  Ile  Val  Gly  Ser  Pro  Glu  Leu  Thr  Phe
                    245                      250                      255

Gly  Lys  Gly  Thr  Gln  Leu  Ser  Val  Val  Asp  Tyr  Lys  Asp  Asp  Asp  Asp
               260                      265                      270

Lys
```

( 2 ) INFORMATION FOR SEQ ID NO:13:

( i ) SEQUENCE CHARACTERISTICS:
        ( A ) LENGTH: 371 base pairs
        ( B ) TYPE: nucleic acid
        ( C ) STRANDEDNESS: single
        ( D ) TOPOLOGY: linear ( i x ) FEATURE:
        ( A ) NAME/KEY: mat_peptide
        ( B ) LOCATION: 1..363

( i x ) FEATURE:
        ( A ) NAME/KEY: CDS
        ( B ) LOCATION: 1..363

( x i ) SEQUENCE DESCRIPTION: SEQ ID NO:13:

```
ATG  AAA  TAC  CTA  TTG  CCT  ACG  GCA  GCC  GCT  GGA  TTG  TTA  TTA  CTC  GCT     48
Met  Lys  Tyr  Leu  Leu  Pro  Thr  Ala  Ala  Ala  Gly  Leu  Leu  Leu  Leu  Ala
1              5                        10                       15

GCC  CAA  CCA  GCG  ATG  GCC  AAG  GCC  CAT  GTC  ACC  CAT  CAC  CGC  AGA  CCT     96
Ala  Gln  Pro  Ala  Met  Ala  Lys  Ala  His  Val  Thr  His  His  Arg  Arg  Pro
               20                       25                       30

GAA  GGT  GAT  GTC  ACC  CTG  AGG  TGC  TGG  GCC  CTG  GGC  TTC  TAC  CCT  GCT    144
Glu  Gly  Asp  Val  Thr  Leu  Arg  Cys  Trp  Ala  Leu  Gly  Phe  Tyr  Pro  Ala
          35                       40                       45

GAC  ATC  ACC  CTG  ACC  TGG  CAG  TTG  AAT  GGG  GAC  GAG  CTG  ACC  CAG  GAA    192
Asp  Ile  Thr  Leu  Thr  Trp  Gln  Leu  Asn  Gly  Asp  Glu  Leu  Thr  Gln  Glu
```

```
ATG GAG CTT GTG GAG ACC AGG CCT GCA GGG GAT GGA ACC TTC CAG AAG      240
Met Glu Leu Val Glu Thr Arg Pro Ala Gly Asp Gly Thr Phe Gln Lys
 65                  70                  75                  80

TGG GCA TCT GTG GTG GTG CCT CTT GGG AAG GAG CAG AAG TAC ACA TGC      288
Trp Ala Ser Val Val Val Pro Leu Gly Lys Glu Gln Lys Tyr Thr Cys
                 85                  90                  95

CAT GTG GAA CAT GAG GGG CTG CCT GAG CCC CTC ACC CTG AGA TGG GGC      336
His Val Glu His Glu Gly Leu Pro Glu Pro Leu Thr Leu Arg Trp Gly
             100                 105                 110

AAG GAG GAG CCT CCT TCA TCC ACC AAG TAGAATTC                         371
Lys Glu Glu Pro Pro Ser Ser Thr Lys
         115                 120
```

( 2 ) INFORMATION FOR SEQ ID NO:14:

( i ) SEQUENCE CHARACTERISTICS:
        ( A ) LENGTH: 121 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Lys Tyr Leu Leu Pro Thr Ala Ala Ala Gly Leu Leu Leu Leu Ala
 1                   5                  10                  15

Ala Gln Pro Ala Met Ala Lys Ala His Val Thr His His Arg Arg Pro
                 20                  25                  30

Glu Gly Asp Val Thr Leu Arg Cys Trp Ala Leu Gly Phe Tyr Pro Ala
             35                  40                  45

Asp Ile Thr Leu Thr Trp Gln Leu Asn Gly Asp Glu Leu Thr Gln Glu
         50                  55                  60

Met Glu Leu Val Glu Thr Arg Pro Ala Gly Asp Gly Thr Phe Gln Lys
 65                  70                  75                  80

Trp Ala Ser Val Val Val Pro Leu Gly Lys Glu Gln Lys Tyr Thr Cys
                 85                  90                  95

His Val Glu His Glu Gly Leu Pro Glu Pro Leu Thr Leu Arg Trp Gly
             100                 105                 110

Lys Glu Glu Pro Pro Ser Ser Thr Lys
         115                 120
```

( 2 ) INFORMATION FOR SEQ ID NO:15:

( i ) SEQUENCE CHARACTERISTICS:
        ( A ) LENGTH: 870 base pairs
        ( B ) TYPE: nucleic acid
        ( C ) STRANDEDNESS: single
        ( D ) TOPOLOGY: linear ( i x ) FEATURE:
        ( A ) NAME/KEY: mat_peptide
        ( B ) LOCATION: 40..834

( i x ) FEATURE:
        ( A ) NAME/KEY: CDS
        ( B ) LOCATION: 40..834

( x i ) SEQUENCE DESCRIPTION: SEQ ID NO:15:

```
AAGCTTGCAT GCAAATTCTA TTTCAAGGAG ACAGTCATA ATG AAA TAC CTA TTG        54
                                           Met Lys Tyr Leu Leu
                                            1                 5

CCT ACG GCA GCC GCT GGA TTG TTA TTA CTC GCG GCC CAG CCG GCC ATG      102
Pro Thr Ala Ala Ala Gly Leu Leu Leu Leu Ala Ala Gln Pro Ala Met
                 10                  15                  20
```

```
GCC GAG GTG AAG CTG CAG GAG TCT GGA GGT GGC CCG GTA CAA CCT GGA      150
Ala Glu Val Lys Leu Gln Glu Ser Gly Gly Gly Pro Val Gln Pro Gly
         25                  30                  35

GGA TCC CTG AAA CTC TCC TGT GCA GCC TCA GGA TTC GAT TTT AGT AGA      198
Gly Ser Leu Lys Leu Ser Cys Ala Ala Ser Gly Phe Asp Phe Ser Arg
         40                  45                  50

TAC TGG ATG AAT TGG GTC CGG CGG GCT CCA GGG AAG GGG CTA GAG TGG      246
Tyr Trp Met Asn Trp Val Arg Arg Ala Pro Gly Lys Gly Leu Glu Trp
         55                  60                  65

ATT GGA GAA ATT AAT CAA CAA AGC AGT ACG ATA AAC TAT TCG CCA CCT      294
Ile Gly Glu Ile Asn Gln Gln Ser Ser Thr Ile Asn Tyr Ser Pro Pro
 70                  75                  80                  85

CTG AAG GAT AAA TTC ATC ATC TCC AGA GAC AAC GCC AAA AGT ACG CTG      342
Leu Lys Asp Lys Phe Ile Ile Ser Arg Asp Asn Ala Lys Ser Thr Leu
                 90                  95                 100

TAC CTG CAA ATG AAC AAA GTG AGA TCT GAG GAC ACA GCC TTA TAT TAT      390
Tyr Leu Gln Met Asn Lys Val Arg Ser Glu Asp Thr Ala Leu Tyr Tyr
                105                 110                 115

TGT GCA AGA CTT TCT CTT ACT GCG GCA GGG TTT GCT TAC TGG GGC CAA      438
Cys Ala Arg Leu Ser Leu Thr Ala Ala Gly Phe Ala Tyr Trp Gly Gln
        120                 125                 130

GGG ACT CTG GTC ACC GTC GCC TCC GAC ATC GTC ATG TCA CAG TCT CCA      486
Gly Thr Leu Val Thr Val Ala Ser Asp Ile Val Met Ser Gln Ser Pro
135                 140                 145

TCC TCC CTG GCT GTG TCA GTA GGA GAG AAG GTC ACT ATG AGC TGC AGA      534
Ser Ser Leu Ala Val Ser Val Gly Glu Lys Val Thr Met Ser Cys Arg
150                 155                 160                 165

TCC AGT CAG AGT CTG TTC AAC AGT AGA ACC CGA AAG AAC TAC TTG ACT      582
Ser Ser Gln Ser Leu Phe Asn Ser Arg Thr Arg Lys Asn Tyr Leu Thr
                170                 175                 180

TGG TAC CAG CAG AAA CCA GGG CAG TCT CCT AAA CCG CTG ATC TAC TGG      630
Trp Tyr Gln Gln Lys Pro Gly Gln Ser Pro Lys Pro Leu Ile Tyr Trp
        185                 190                 195

GCA TCC ACT AGG GAA TCT GGG GTC CCT GAT CGC TTC ACA GGC AGT GGA      678
Ala Ser Thr Arg Glu Ser Gly Val Pro Asp Arg Phe Thr Gly Ser Gly
        200                 205                 210

TCT GGG ACA GAT TTC ACT CTC ACC ATC AGC AGT GTG CAG GCT GAA GAC      726
Ser Gly Thr Asp Phe Thr Leu Thr Ile Ser Ser Val Gln Ala Glu Asp
215                 220                 225

CTG GCA GAT TAT TAC TGC AAG CAA TCT TAT AAT CTT CGG ACG TTC GGT      774
Leu Ala Asp Tyr Tyr Cys Lys Gln Ser Tyr Asn Leu Arg Thr Phe Gly
230                 235                 240                 245

GGA GGC ACC AAG CTG GAA ATT AAT CGG GCG GCC GCA GAT TAT AAA GAT      822
Gly Gly Thr Lys Leu Glu Ile Asn Arg Ala Ala Ala Asp Tyr Lys Asp
                250                 255                 260

GAT GAT GAT AAA TAGGCCGCAT AGACTGTTGA AAGTTGTTTA GCAAAA           870
Asp Asp Asp Lys
        265
```

(2) INFORMATION FOR SEQ ID NO:16:

(i) SEQUENCE CHARACTERISTICS:
        (A) LENGTH: 265 amino acids
        (B) TYPE: amino acid
        (D) TOPOLOGY: linear (ii) MOLECULE TYPE: protein (xi) SEQUENCE DESCRIPTION: SEQ ID NO:16:

```
Met Lys Tyr Leu Leu Pro Thr Ala Ala Ala Gly Leu Leu Leu Leu Ala
 1               5                  10                  15
```

| | | | | | | | | | | | | | | |
|---|---|---|---|---|---|---|---|---|---|---|---|---|---|---|
| Ala | Gln | Pro | Ala | Met | Ala | Glu | Val | Lys | Leu | Gln | Glu | Ser | Gly | Gly | Gly |
| | | | 20 | | | | 25 | | | | | 30 | | |
| Pro | Val | Gln | Pro | Gly | Gly | Ser | Leu | Lys | Leu | Ser | Cys | Ala | Ala | Ser | Gly |
| | | 35 | | | | 40 | | | | | 45 | | | |
| Phe | Asp | Phe | Ser | Arg | Tyr | Trp | Met | Asn | Trp | Val | Arg | Arg | Ala | Pro | Gly |
| | 50 | | | | | 55 | | | | | 60 | | | | |
| Lys | Gly | Leu | Glu | Trp | Ile | Gly | Glu | Ile | Asn | Gln | Ser | Ser | Thr | Ile |
| 65 | | | | | 70 | | | | | 75 | | | | 80 |
| Asn | Tyr | Ser | Pro | Pro | Leu | Lys | Asp | Lys | Phe | Ile | Ile | Ser | Arg | Asp | Asn |
| | | | | 85 | | | | | 90 | | | | | 95 | |
| Ala | Lys | Ser | Thr | Leu | Tyr | Leu | Gln | Met | Asn | Lys | Val | Arg | Ser | Glu | Asp |
| | | | 100 | | | | | 105 | | | | | 110 | | |
| Thr | Ala | Leu | Tyr | Tyr | Cys | Ala | Arg | Leu | Ser | Leu | Thr | Ala | Ala | Gly | Phe |
| | | 115 | | | | | 120 | | | | | 125 | | | |
| Ala | Tyr | Trp | Gly | Gln | Gly | Thr | Leu | Val | Thr | Val | Ala | Ser | Asp | Ile | Val |
| | 130 | | | | | 135 | | | | | 140 | | | | |
| Met | Ser | Gln | Ser | Pro | Ser | Ser | Leu | Ala | Val | Ser | Val | Gly | Glu | Lys | Val |
| 145 | | | | | 150 | | | | | 155 | | | | | 160 |
| Thr | Met | Ser | Cys | Arg | Ser | Ser | Gln | Ser | Leu | Phe | Asn | Ser | Arg | Thr | Arg |
| | | | | 165 | | | | | 170 | | | | | 175 | |
| Lys | Asn | Tyr | Leu | Thr | Trp | Tyr | Gln | Gln | Lys | Pro | Gly | Gln | Ser | Pro | Lys |
| | | | | 180 | | | | | 185 | | | | | 190 | |
| Pro | Leu | Ile | Tyr | Trp | Ala | Ser | Thr | Arg | Glu | Ser | Gly | Val | Pro | Asp | Arg |
| | | | 195 | | | | | 200 | | | | | 205 | | |
| Phe | Thr | Gly | Ser | Gly | Ser | Gly | Thr | Asp | Phe | Thr | Leu | Thr | Ile | Ser | Ser |
| | | 210 | | | | | 215 | | | | | 220 | | | |
| Val | Gln | Ala | Glu | Asp | Leu | Ala | Asp | Tyr | Tyr | Cys | Lys | Gln | Ser | Tyr | Asn |
| 225 | | | | | 230 | | | | | 235 | | | | | 240 |
| Leu | Arg | Thr | Phe | Gly | Gly | Gly | Thr | Lys | Leu | Glu | Ile | Asn | Arg | Ala | Ala |
| | | | | 245 | | | | | 250 | | | | | 255 | |
| Ala | Asp | Tyr | Lys | Asp | Asp | Asp | Asp | Lys |
| | | | 260 | | | | | 265 |

(2) INFORMATION FOR SEQ ID NO:17:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ix) FEATURE:
        (A) NAME/KEY: mat_peptide
        (B) LOCATION: 1..819

(ix) FEATURE:
        (A) NAME/KEY: CDS
        (B) LOCATION: 1..819

(xi) SEQUENCE DESCRIPTION: SEQ ID NO:17:

| | | | | | | | | | | | | | | | |
|---|---|---|---|---|---|---|---|---|---|---|---|---|---|---|---|
| ATG | AAA | TAC | CTA | TTG | CCT | ACG | GCA | GCC | GCT | GGA | TTG | TTA | TTA | CTC | GCT | 48 |
| Met | Lys | Tyr | Leu | Leu | Pro | Thr | Ala | Ala | Ala | Gly | Leu | Leu | Leu | Leu | Ala | |
| 1 | | | | 5 | | | | | 10 | | | | | 15 | | |
| GCC | CAA | CCA | GCG | ATG | GCG | CAG | GTG | CAG | CTG | CAG | CAG | TCT | GGG | GCT | GAA | 96 |
| Ala | Gln | Pro | Ala | Met | Ala | Gln | Val | Gln | Leu | Gln | Gln | Ser | Gly | Ala | Glu | |
| | | | 20 | | | | 25 | | | | | 30 | | | | |
| CTG | GTG | AAG | CCT | GGG | GCC | TCA | GTG | AGG | ATG | TCC | TGC | AAG | GCT | TCT | GGC | 144 |
| Leu | Val | Lys | Pro | Gly | Ala | Ser | Val | Arg | Met | Ser | Cys | Lys | Ala | Ser | Gly | |
| | | 35 | | | | | 40 | | | | | 45 | | | | |
| TAC | ACA | TTT | ACC | AAT | TAC | AAC | ATG | TAC | TGG | GTA | AAA | CAG | TCA | CCT | GGA | 192 |

| | | | | | | | | | | | | | | | |
|---|---|---|---|---|---|---|---|---|---|---|---|---|---|---|---|
|Tyr|Thr|Phe|Thr|Asn|Tyr|Asn|Met|Tyr|Trp|Val|Lys|Gln|Ser|Pro|Gly|
| |50| | | |55| | | | |60| | | | | |

```
CAG  GGC  CTG  GAG  TGG  ATT  GGA  ATT  TTT  TAT  CCA  GGA  AAT  GGT  GAT  ACT    240
Gln  Gly  Leu  Glu  Trp  Ile  Gly  Ile  Phe  Tyr  Pro  Gly  Asn  Gly  Asp  Thr
 65            70                      75                           80

TCC  TAC  AAT  CAG  AAG  TTC  AAA  GAC  AAG  GCC  ACA  TTG  ACT  GCT  GAC  AAA    288
Ser  Tyr  Asn  Gln  Lys  Phe  Lys  Asp  Lys  Ala  Thr  Leu  Thr  Ala  Asp  Lys
                85                      90                           95

TCC  TCC  AAC  ACA  GCC  TAC  ATG  CAG  CTC  AGC  AGC  CTG  ACA  TCT  GAG  GAC    336
Ser  Ser  Asn  Thr  Ala  Tyr  Met  Gln  Leu  Ser  Ser  Leu  Thr  Ser  Glu  Asp
               100                     105                          110

TCT  GCG  GTC  TAT  TAC  TGT  GCA  AGA  TCG  GGG  GGC  TCC  TAT  AGA  TAC  GAC    384
Ser  Ala  Val  Tyr  Tyr  Cys  Ala  Arg  Ser  Gly  Gly  Ser  Tyr  Arg  Tyr  Asp
               115                     120                          125

GGA  GGC  TTT  GAC  TAC  TGG  GGC  CAA  GGG  ACC  ACG  GTC  ACC  GTC  TCC  GGT    432
Gly  Gly  Phe  Asp  Tyr  Trp  Gly  Gln  Gly  Thr  Thr  Val  Thr  Val  Ser  Gly
     130                     135                          140

GGT  GGT  GGT  TCG  GGT  GGT  GGT  GGT  TCG  GGT  GGT  GGT  GGT  TCG  GAT  ATC    480
Gly  Gly  Gly  Ser  Gly  Gly  Gly  Gly  Ser  Gly  Gly  Gly  Gly  Ser  Asp  Ile
145                     150                          155                     160

GAG  CTC  ACA  CAG  ACT  ACA  TCC  TCC  CTG  TCT  GCC  TCT  CTG  GGA  GAC  AGA    528
Glu  Leu  Thr  Gln  Thr  Thr  Ser  Ser  Leu  Ser  Ala  Ser  Leu  Gly  Asp  Arg
          165                     170                          175

GTC  ACC  ATC  AGT  TGC  AGG  GCA  AGT  CAG  GAC  ATT  AGT  AAT  TAT  TTA  AAC    576
Val  Thr  Ile  Ser  Cys  Arg  Ala  Ser  Gln  Asp  Ile  Ser  Asn  Tyr  Leu  Asn
               180                     185                          190

TGG  TAT  CAA  CAG  AAT  CCA  GAT  GGA  ACT  GTT  AAA  CTC  CTG  ATC  TAC  TAC    624
Trp  Tyr  Gln  Gln  Asn  Pro  Asp  Gly  Thr  Val  Lys  Leu  Leu  Ile  Tyr  Tyr
               195                     200                          205

ACA  TCA  AAT  TTA  CAC  TCA  GAA  GTC  CCA  TCA  CGG  TTC  AGT  GGC  AGT  GGG    672
Thr  Ser  Asn  Leu  His  Ser  Glu  Val  Pro  Ser  Arg  Phe  Ser  Gly  Ser  Gly
     210                     215                          220

TCT  GGA  ACA  GAT  TAT  TCT  CTC  ACC  ATT  AGC  AAC  CTG  GAA  CAA  GAA  GAT    720
Ser  Gly  Thr  Asp  Tyr  Ser  Leu  Thr  Ile  Ser  Asn  Leu  Glu  Gln  Glu  Asp
225                     230                          235                     240

ATT  GCC  ACT  TAC  TTT  TGC  CAA  CAG  GAT  TTT  ACG  CTT  CCG  TTC  ACG  TTC    768
Ile  Ala  Thr  Tyr  Phe  Cys  Gln  Gln  Asp  Phe  Thr  Leu  Pro  Phe  Thr  Phe
                    245                     250                          255

GGA  GGG  GGG  ACC  AAG  CTC  GAG  ATA  AGA  GAC  TAC  AAA  GAC  GAT  GAC  GAT    816
Gly  Gly  Gly  Thr  Lys  Leu  Glu  Ile  Arg  Asp  Tyr  Lys  Asp  Asp  Asp  Asp
               260                     265                          270

AAA  TAATAAGAAT TC                                                                 831
Lys
```

( 2 ) INFORMATION FOR SEQ ID NO:18:

( i ) SEQUENCE CHARACTERISTICS:
        ( A ) LENGTH: 273 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met  Lys  Tyr  Leu  Leu  Pro  Thr  Ala  Ala  Ala  Gly  Leu  Leu  Leu  Leu  Ala
 1              5                      10                          15

Ala  Gln  Pro  Ala  Met  Ala  Gln  Val  Gln  Leu  Gln  Gln  Ser  Gly  Ala  Glu
               20                     25                          30

Leu  Val  Lys  Pro  Gly  Ala  Ser  Val  Arg  Met  Ser  Cys  Lys  Ala  Ser  Gly
          35                     40                          45

Tyr  Thr  Phe  Thr  Asn  Tyr  Asn  Met  Tyr  Trp  Val  Lys  Gln  Ser  Pro  Gly
```

|   |   |   |   |   | 50 |   |   |   |   | 55 |   |   |   |   | 60 |   |   |   |   |
|---|---|---|---|---|---|---|---|---|---|---|---|---|---|---|---|---|---|---|---|

Gln Gly Leu Glu Trp Ile Gly Ile Phe Tyr Pro Gly Asn Gly Asp Thr
65                  70                  75                  80

Ser Tyr Asn Gln Lys Phe Lys Asp Lys Ala Thr Leu Thr Ala Asp Lys
                85                  90                  95

Ser Ser Asn Thr Ala Tyr Met Gln Leu Ser Ser Leu Thr Ser Glu Asp
            100                 105                 110

Ser Ala Val Tyr Tyr Cys Ala Arg Ser Gly Gly Ser Tyr Arg Tyr Asp
        115                 120                 125

Gly Gly Phe Asp Tyr Trp Gly Gln Gly Thr Thr Val Thr Val Ser Gly
    130                 135                 140

Gly Gly Gly Ser Gly Gly Gly Gly Ser Gly Gly Gly Ser Asp Ile
145                 150                 155                 160

Glu Leu Thr Gln Thr Thr Ser Ser Leu Ser Ala Ser Leu Gly Asp Arg
                165                 170                 175

Val Thr Ile Ser Cys Arg Ala Ser Gln Asp Ile Ser Asn Tyr Leu Asn
            180                 185                 190

Trp Tyr Gln Gln Asn Pro Asp Gly Thr Val Lys Leu Leu Ile Tyr Tyr
        195                 200                 205

Thr Ser Asn Leu His Ser Glu Val Pro Ser Arg Phe Ser Gly Ser Gly
    210                 215                 220

Ser Gly Thr Asp Tyr Ser Leu Thr Ile Ser Asn Leu Glu Gln Glu Asp
225                 230                 235                 240

Ile Ala Thr Tyr Phe Cys Gln Gln Asp Phe Thr Leu Pro Phe Thr Phe
                245                 250                 255

Gly Gly Gly Thr Lys Leu Glu Ile Arg Asp Tyr Lys Asp Asp Asp Asp
            260                 265                 270

Lys ( 2 ) INFORMATION FOR SEQ ID NO:19:

( i ) SEQUENCE CHARACTERISTICS:
        ( A ) LENGTH: 1443 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
AAAAAAGCGG CCCAGCCGGC CATGGCCGAG GTGAGGCTTC TCGAGTCTGG AGGTGGCCCG      60
GTACAACCTG GAGGATCCCT GAAACTCTCC TGTGCAGCCT CAGGATTCGA TTTTAGTAGA    120
TACTGGATGA ATTGGGTCCG GCGGGCTCCA GGGAAGGGGC TAGAGTGGAT TGGAGAAATT    180
AATCAACAAA GCAGTACGAT AAACTATTCG CCACCTCTGA AGGATAAATT CATCATCTCC    240
AGAGACAACG CCAAAAGTAC GCTGTACCTG CAAATGAACA AAGTGAGATC TGAGGACACA    300
GCCCTTTATT ATTGTGCAAG ACTTTCTCTT ACTGCGGCAG GGTTTGCTTA CTGGGGCCAA    360
GGGACTCTGG TCACTGTCTC TGCAGCCAAA ACGACACCCC CATCTGTCTA TCCACTGGCC    420
CCTGGATCTG CTGCCCAAAC TAACTCCATG GTGACCCTGG GATGCCTGGT CAAGGGCTAT    480
TTCCCTGAGC CAGTGACAGT GACCTGGAAC TCTGGATCCC TGTCCAGCGG TGTGCACACC    540
TTCCCAGCTG TCCTGCAGTC TGACCTCTAC ACTCTGAGCA GCTCAGTGAC TGTCCCCTCC    600
AGCACCTGGC CCAGCGAGAC CGTCACCTGC AACGTTGCCC ACCCGGCCAG CAGCACCAAG    660
GTGGACAAGA AAATTGAAGA ATTTTAATTA AAACATGGAA ATAAAGTGAA ACAAAGCACT    720
ATTGCACTGG CACTCTTACC GTTACTCTTT ACCCCGGTAA CCAAAGCCGA CATCGTCATG    780
```

-continued

| | | | | | | |
|---|---|---|---|---|---|---|
|TCACAGTCTC|CATCCTCCCT|GGCTGTGTCA|GTAGGAGAGA|AGGTCACTAT|GAGCTGCAGA|840|
|TCCAGTCAGA|GTCTGTTCAA|CAGTAGAACC|CGAAAGAACT|ACTTGACTTG|GTACCAGCAG|900|
|AAACCAGGGC|AGTCTCCTAA|ACCGCTGATC|TACTGGGCAT|CCACTAGGGA|ATCTGGGGTC|960|
|CCTGATCGCT|TCACAGGCAG|TGGATCTGGG|ACAGATTTCA|CTCTCACCAT|CAGCAGTGTG|1020|
|CAGGCTGAAG|ACCTGGCAGA|TTATTACTGC|AAGCAATCTT|ATAATCTTCG|GACGTTCGGT|1080|
|GGAGGCACCA|AGCTGGAAAT|TAAACGGGCT|GATGCTGCAG|TATCCATCTT|CCCACCATCC|1140|
|AGTGAGCAGT|TAACATCTGG|ATCTGGAGGT|GCCTCAGTCG|TGTGCTTCTT|GAACAACTTC|1200|
|TACCCCAAAG|ACATCAATGT|CAAGTGGAAG|ATTGATGGCA|GTGAACGACA|AAATGGCGTC|1260|
|CTGAACAGTT|GGACTGATCA|GGACAGCAAA|GACAGCACCT|ACAGCATGAG|CAGCACCCTC|1320|
|ACGTTGACCA|AGGACGAGTA|TGAACGACAT|AACAGCTATA|CCTGTGAGGC|CACTCACAAG|1380|
|ACATCAACTT|CACCCATTGT|CAAGAGCTTC|AACAGGGGAG|AGTGTGCGGC|CGCAGATTAT|1440|
|AAA| | | | | |1443|

( 2 ) INFORMATION FOR SEQ ID NO:20:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GTCACCGTCT CCGGTGGTGG TGGTTCGGAT ATCGAGCT        38

( 2 ) INFORMATION FOR SEQ ID NO:21:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GTCACCGTCT CCGGTGGTGG TGGTTCGGAT ATCCAGCT        38

( 2 ) INFORMATION FOR SEQ ID NO:22:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GTCACCGTCT CCGGTGGTGG TGGTTCGGAT ATCGAGCT        38

( 2 ) INFORMATION FOR SEQ ID NO:23:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GTCACCGTCT CCGATATCGA GCT        23

( 2 ) INFORMATION FOR SEQ ID NO:24:

( i ) SEQUENCE CHARACTERISTICS:

(A) LENGTH: 48 base pairs
(B) TYPE: nucleic acid
(C) STRANDEDNESS: single
(D) TOPOLOGY: linear (xi) SEQUENCE DESCRIPTION: SEQ ID NO:24:

GGGACCACGG TCACCGTCTC CTCAGCCTCT CTGGGAGACA GAGTCACC    48

(2) INFORMATION FOR SEQ ID NO:25:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:25:

GTCGACGAAT TCTTATTATT TATCGTCATC ATCTTTGTAG TC    42

TARGET BINDING POLYPEPTIDE

This invention relates to the construction, application and production of novel polypeptides with enhanced or modified binding activity or specificity to haptens and antigens.

The invention also relates to the construction, modification and selection of recombinant antibody-like molecules derived from expression of libraries of surface presenting antigen- or hapten-binding moieties, and to uses of these molecules.

The polypeptides of the invention have utility in the diagnostic, therapeutic, predictive or preventative fields of the pharmaceutical and health care industries, as well as more general application in the detection and assay of chemical entities.

BACKGROUND OF THE INVENTION

Antibodies are protein molecules which possess a binding affinity for a target antigen or hapten. Due to the specificity of the binding interaction, antibodies are commonly used as diagnostic and therapeutic reagents. Monoclonal antibodies are derived from a pure cell line such as hybridoma cells; however, the hybridoma technology is expensive, time-consuming to maintain and limited in scope. It is not possible to produce monoclonal antibodies, much less antibodies of the appropriate affinity, to a complete range of antigens.

Antibody genes or fragments thereof can be cloned and expressed in E. coli in a biologically functional form. Antibodies and antibody fragments can also be produced by recombinant DNA technology using either bacterial or mammalian cells. In the Fab region of an antibody, the combination of the two heavy and light chains provides six variable surface loops at the extremity of the molecule. These loops in the outer domain (Fv) are termed complementarity-determining-regions (CDRs), and provide the specificity of binding of the antibody to its antigenic target. This binding function is localised to the variable domains of the antibody molecule, which are located at the amino-terminal end of both the heavy and light chains. This is illustrated in FIG. 1. The variable regions of some antibodies remain non-covalently associated (as $V_H V_L$ dimers, termed Fv regions) even after proteolytic cleavage from the native antibody molecule, and retain much of their antigen recognition and binding capabilities. Methods of manufacture of two-chain Fv substantially free of constant region are disclosed in U.S. Pat. No. 4,642,334

Recombinant Fv fragments are prone to dissociation, and therefore some workers have chosen to covalently link the two domains to form a construct designated scFv, in which two peptides with binding domains (usually antibody heavy and light variable regions) are joined by a linker peptide connecting the C-terminus of one domain to the N-terminus of the other, so that the relative positions of the antigen binding domains are consistent with those found in the original antibody (see FIG. 1).

Methods of manufacture of covalently linked Fv fragments are disclosed in U.S. Pat. No. 4,946,778 and U.S. Pat. No. 5,132,405. Further heterogeneity can be achieved by the production of bifunctional and multifunctional agents (Huston et al U.S. Pat. No. 5,091,513, and Ladner et al U.S. Pat. No. 4,816,397).

The construction of scFv libraries is disclosed for example in European Patent Application No. 239400 and U.S. Pat. No. 4,946,778. However, single-chain Fv libraries are limited in size because of problems inherent in the cloning of a single DNA molecule encoding the scFv. Non-scFv libraries, such as $V_H$ or Fab libraries, are also known, (Ladner and Guterman WO 90/02809), and may be used with a phage system for surface expression (Ladner et al WO 88/06630 and Bonnert et al at WO 92/01047).

For use in antibody therapy, monoclonal antibodies, which are usually of mouse origin, have limited use unless they are first "humanised", because they elicit an antigenic response on administration to humans. The variable domains of an antibody consist of a β-sheet framework with six hypervariable regions (CDRs) which fashion the antigen-binding site. Humanisation consists of substituting mouse sequences that provide the binding affinity, particularly the CDR loop sequences, into a human variable domain structure. The murine CDR loop regions can therefore provide the binding affinities for the required antigen. Recombinant antibody "humanisation" by grafting of CDRs is disclosed by Winter et al (EP-239400).

The expression of diverse recombinant human antibodies by the use of expression/combinatorial systems has been described. (Marks et al, J. Mol. Biol. 1991 222 581–597). Recent developments in methods for the expression of peptides and proteins on the surface of filamentous phage (McCafferty et al, Nature 1991 348 552; Clackson et al, J. Mol. Biol., 1991 352 624–28) offer the potential for the selection, improvement and development of these reagents as diagnostics and therapeutics. The use of modified bacteriophage genomes for the expression, presentation and pairing of cloned heavy and light chain genes of both mouse and human origins has been described (Hoogenboom et al, Nucl. Acids. Res., 19 4133–4137; Marks et al 1991 op. cit. and Bonnert et al, WPI Acc. No. 92-056862/07)

Receptor molecules, whose expression is the result of the receptor-coding gene library in the expressing organism, may also be displayed in the same way (Lerner and Sorge, WO 90/14430). The cell surface expression of single chain antibody domains fused to a cell surface protein is disclosed by Ladner et al WO 88/06630.

Affinity maturation is a process whereby the binding specificity, affinity or avidity of an antibody can be modified. A number of laboratory techniques have been devised whereby amino acid sequence diversity is created by the application of various mutation strategies, either on the entire antibody fragment or on selected regions such as the CDRs. Mutation to change enzyme specific activity has also been reported. The person skilled in the art will be aware of a variety of methods for achieving random or site-directed mutagenesis, and for selecting molecules with a desired modification. Mechanisms to increase diversity and to select specific antibodies by the so called "chain shuffling" technique, ie. the reassortment of a library of one chain type e.g. heavy chain, with a fixed complementary chain, such as light chain, have also been described (Kang et al, Proc. Natl. Acad. Sci. USA, 1991 88 4363–466; Hoogenboom et al, Nucl. Acid Res., 1991 19 4133–4137; Marks et al, Bio/Technology, 1992 10 779–783).

In order to overcome the problems of human reactions to murine sequences in any part of the V-domains, framework or constant regions of the antibodies, recombinant human antibody-gene libraries may be constructed from a variety of human tissues, including peripheral blood lymphocytes (Winter and Milstein Nature, 1991 349 293). Adult humans will already have been subjected to antigenic stimulation, and therefore the capacity of the pre-immunised adult B-cell population to recognise as wide a range of antigens is diminished compared to the naive B-cell population, and is reflected in the restricted populations of antibody mRNA molecules.

Thus in order to access as wide a range of antigen-binding potential as possible, one of the tissues of choice is foetal peripheral blood, which being naive has a higher proportion of IgM antibody molecules than adult blood, (approximately 70% compared to the 30% for IgG), and provides the ideal source of genetic material for the construction of an antibody library destined for maturation (evolution) to a breadth where a wide range of antigens can be bound.

SUMMARY OF THE INVENTION

The present invention therefore includes within its scope:
1) The-identification and construction of novel recombinant target binding is polypeptides;
2) Modification of such reagents to alter their performance, for example by mechanisms involving the mutation of their DNA coding regions; and
3) Further changing these reagents either at the genetic or the protein level, by reassortment of their subcomponents.

According to a first aspect, the invention provides a recombinant target-binding polypeptide having:
a) a stable core polypeptide region (SCR); and
b) at least one target-binding region (TBR), in which the target-binding region(s) has optionally been subjected to a maturation step in order to modify the specificity, the affinity or the avidity of binding to the target.

We have been able to design and construct polypeptides according to the invention in which the specificity, affinity or avidity of binding is modified, without the necessity for performing a maturation step. For example this has been done using immunoglobulin (Ig) and CD8.

We describe the construction of monovalent target binding polypeptides in which the TBR is covalently linked to a SCR. The SCR is preferably formed by association of two covalently linked Ig-like domains of the Ig superfamily such as to antibody variable domains or CD8 domains.

We also show how polyfunctional target binding polypeptides can be produced by forming separate or overlapping TBRs on a SCR. We have also shown that the Ig-like domains of members of the Ig superfamily can be constructed as SCRs and joined non-covalently to produce bifunctional or polyfunctional target-binding polypeptides. We describe how to design amino acid sequences which can covalently link Ig-like domains and thereby direct self association to form stable dimers, aggregates or arrays preferably with bifunctional or polyfunctional specificity.

The target-binding region is able to bind a target molecule, which may be a chemical entity of any type. For example, the target may be a small molecule such as a pesticide or a drug, a hormone such as a steroid, an amino acid, a peptide, or a polypeptide; an antigen, such as a bacterial, viral or cell surface antigen; antibodies or other members of the Ig superfamily; a tumour marker, a growth factor, etc. The skilled person will readily be able to select a wide variety of targets of interest.

Where the polypeptide of the invention is to be used for in vitro diagnostic purposes, the core polypeptide region may be any suitable protein. However, where the polypeptide of the invention is intended for use in vivo, the core polypeptide region should preferably be non-antigenic. Thus any normal human protein of the type which is present in serum or displayed on cell surfaces, and is generally tolerated, would be suitable. Certain domains of normal cell-surface proteins can be produced in soluble form and, by the methods of this invention, have their affinity properties enhanced or modified. For human proteins which have as their natural target T-cell surface proteins, the soluble fragments become potential immunomodulatory therapeutic reagents especially useful for transplantation. May of these fragments will possess homology to proteins of the immmoglobulin superfamily.

In particularly preferred embodiments of the invention, the target is selected from the group consisting of glycophorin or other red blood cell surface proteins, influenza virus neuraminidase; viral antigens such as hepatitis B antigen, and the gp40 protein of HIV; tumour markers, cell surface proteins such as CD28 and CD4; transforming growth factor $\alpha$ (TGF-$\alpha$); and leukaemia inhibitory factor (LIF). For both diagnostic and therapeutic applications, it is particularly useful if the target binding region has more than one specificity. It is especially preferred that the target binding polypeptide possesses affinity to more than one target; this affinity is provided by separate or overlapping surfaces, thus forming a bifunctional or polyfunctional reagent. It is envisaged that bifunctional or polyfunctional reagents can also be formed by covalent or non-covalent attachment of individual target binding polypeptides, optionally using a linker polypeptide.

In a second aspect, the invention provides a DNA construct encoding the target binding polypeptide.

In a third aspect, the invention provides a method for producing a DNA construct encoding a target binding polypeptide of the invention, comprising the steal of subjecting DNA encoding a target binding polypeptide to one or more cycles of mutagenesis and selection to obtain a sub-population of DNA molecules encoding target binding polypeptides having modified characteristics of affinity, specificity, or avidity.

Preferably the DNA encoding the target binding polypeptide is present in a replication-competent element or display vector, ie. a vector which is self-replicating, optionally when present in a suitable host. The display vector is preferably selected from the group consisting of bacteriophage, filamentous bacteriophages such as Fd, viruses, bacteria, yeast, slime moulds, or mammalian cells.

Mutagenesis may be either random or site-directed, and the person skilled in the art will be aware of many suitable methods for carrying out this step. One or more target binding regions of the target binding polypeptide may be subjected to mutagenesis.

A preferred mutation system for use in the invention utilises specific mutator strains of *Escherichia coli*, designated mutD and mutT1 (R. Fowler et al, J. Bacteriol., 1986 167 130). These particular mutator strains permit transfection with phage, making them especially useful for the purposes of the invention.

In a preferred embodiment, the method of producing the target binding polypeptide comprises the steps of:
a) isolating DNA encoding the framework structure of one or more desired target-binding polypeptides by means of the polymerase chain reaction;
b) optionally subjecting the DNA to mutagenesis in order to induce mutations in one or more target binding regions of the target binding polypeptide;
c) inserting the DNA into one or more display vectors;
d) selecting a sub-population of display vectors displaying target binding polypeptides of desired specificity, avidity or affinity;
e) subjecting the selected sub-population to one or more cycles of mutagenesis and selection in order to obtain a sub-population of display vectors displaying target binding polypeptides having modified characteristics of affinity, specificity or avidity; and f) inserting DNA encoding the modified target binding polypeptides into a high level expression vector.

Selection of the sub-population of display vectors may be achieved by a variety of conventional methods such as target binding, fluorescence-activated cell sorting, or exploitation of the biotin-avidin or biotin-streptavidin systems. A particularly preferred method is affinity selection on an insoluble support such as imnmotubes; this has been found to be especially convenient.

It will be appreciated that the invention therefore also provides a method of producing the target binding polypeptide, by transferring the high level expression vector described above into an appropriate expression host; expressing the target binding polypeptide, and isolating the protein thus produced.

It will also be clearly understood that the target binding regions and the stable core polypeptide may be different regions of the same molecule, or may be derived from different molecules.

Types of target binding polypeptide constructs which are contemplated by the invention include modified antibodies or antibody fragments, scFv fragments comprising an association link to permit continuous reassortment, modified CD8 molecules, for example single chain CD8, and combinations of antibody molecules or fragments thereof with CD8 or other molecules related to the immunoglobulin superfamily such as the individual domains of the MHC Class I and II molecules. For example, the α3 domain of MHC Class I binds to CD8, and therefore soluble versions of α3 become potential immunomodulatory reagents. Preferred constructs utilizing CD8 include:

a) Single-chain molecules in which the V-like domains only of the α and β subunits are linked, and b) Molecules in which the N-terminal amino acid has been altered from lysine to serine, in order to alter the charge balance of the signal peptides, thus enabling bacterial expression without adversely affecting biological activity.

Target binding polypeptides may include covalently attached polypeptide tails which can be TBRS or which may permit non-covalent association to other TBPs.

Although the following description refers in some examples specifically to IgG type antibodies and their fragments, it will be clearly understood that the invention is also applicable to other types of antibody molecule, such as IgM and IgA.

The DNA sequence encoding the target binding polypeptide may be cloned into any vector which will allow display of the polypeptide on bacteriophage or cell surfaces. Preferred vectors include pHFA, whose construction is described in International Patent Application No. PCT/AU93/00228, and its structure is illustrated in FIG. 4. Preferred bacterial hosts for protein expression are *E. coli* and *Bacillus subtilis*.

DETAILED DESCRIPTION OF THE DRAWINGS

The invention will be described in detail by reference to the following non-limiting examples and to the drawings, in which:

FIG. 1 illustrates the structure of antibodies and their fragments:

a) This shows the polypeptide chain structure of a typical IgG antibody molecule, which is composed of two identical heavy and two identical light chains, each divided into variable (V) and constant (C) domains. The whole IgG molecule has two identical antigen binding surfaces termed Fv regions, which are formed by the pairing of $V_H$ and $V_L$ chains. The combination of $V_H$ and $V_L$ provides 6 loops, termed complementarity-determining regions (CDRs), at the extremity of the molecule and these provide the antigen binding surface and thereby the binding specificity of the antibody to its target antigen.

b) an Fab antibody fragment comprises one light and a portion of one heavy chain.

c) A single-chain scFv is shown as $V_H$ and $V_L$ domains joined by a peptide linker between the C-terminus of $V_H$ to the N-terminus of $V_L$. Both Fab and Fv fragments are expected to have the same antigen binding surface as the parent antibody.

FIG. 2 shows antibody fragments such as Fab and scFv molecules displayed on the surface of filamentous Fd bacteriophage by covalent fusion to either the minor coat protein at the tip of the phage, the gene III protein or as fusions with the major, gene VIII coat protein. For display of Fab molecules, only one of the chains (Heavy or Light) is anchored to the phage coat protein, and the other chain is provided in soluble form in the host cell periplasm. The Fd bacteriophage are still viable, although fusions on the gene III protein reduce infectivity into host cells.

FIG. 3 shows how pools (libraries) of heavy and light variable chains can be constructed into a Fd phage display vector with one of the chains fused to either the gene III protein or gene VIII protein of the phage. The display vector is transfected into host cells to generate a dual-combinatorial library. Each host cell produces viable Fd phage in which the antibody fragment is displayed on the phage surface and the gene encoding the antibody is packaged with the viral genome. Affinity purification of the phage is based on affinity to a target antigen, and allows simultaneous recovery of the gene encoding the antibody from the viable phage. Phagemid display vectors can improve transformation yields, but require helper phage to assemble viable progeny. Alternative strategies include the construction of hierarchical libraries in which one chain is held constant and displayed with a library of the second chain to select the highest affinity paired chains. More complex libraries can be constructed using gene pools on separate display vectors and then cross-transfecting host cells. Gene recovery will depend on the relative packing efficiency of the two vectors.

FIG. 4 shows the structure of the phagemid vector pHFA. This vector has the ability in suppressor strains of *E. coli* to express cloned antibodies as fusions with the gene III protein on the surface of the Fd phage, whereas in non-suppressor strains the cloned antibody genes are expressed as soluble products. The lacZ promoter allows induction of expression with IPTG, and the FLAG tail, which is expressed as a fusion with the antibody, is used for detection of synthesis and affinity purification.

FIG. 6 shows the DNA sequence (SEQ ID NOS: 20–25, respectively) of synthetic oligonucleotide duplexes encoding peptide linkers of different lengths that were inserted into appropriately restricted pPOW-scFv NC10.

Figure 7A:
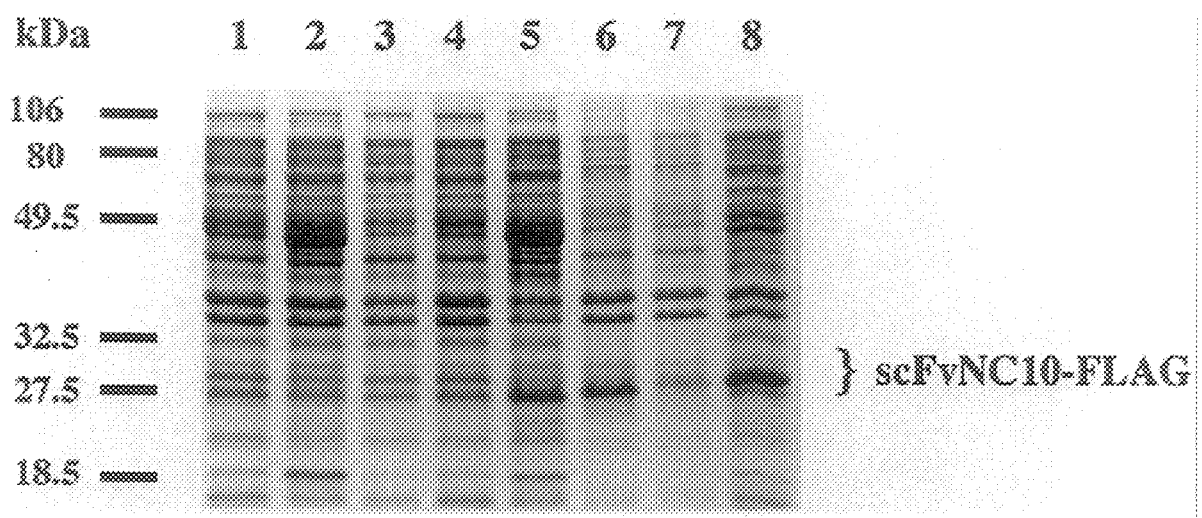
Figure 7B:
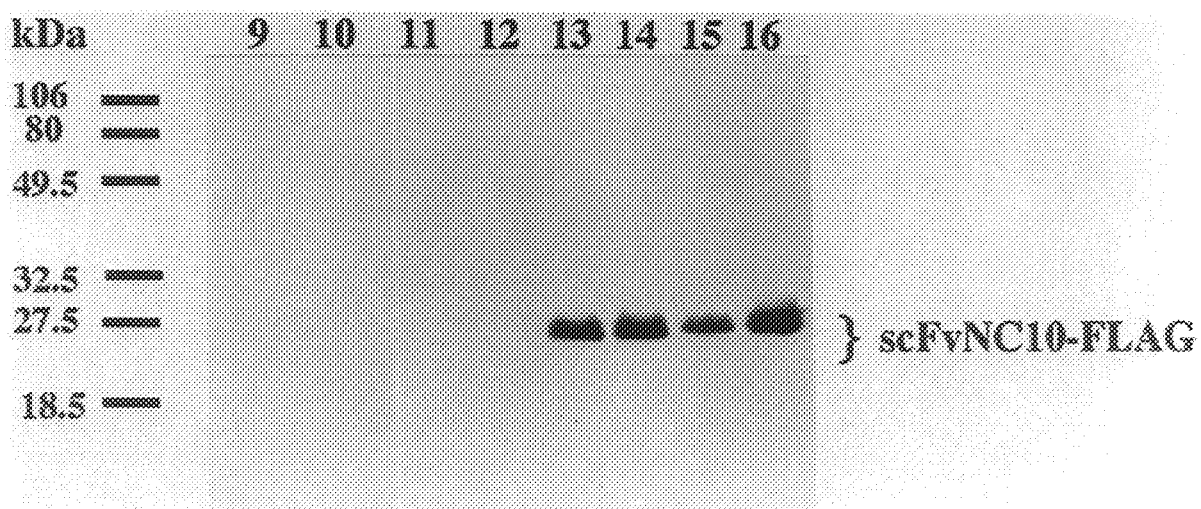

FIG. 7 shows the analysis of synthesised scFv NC10 proteins from the $V_H.15.V_L$, $V_H.10.V_L$, $V_H.5.V_L$ and $V_H.V_L$ from uninduced (lanes 1–4) and induced (lanes 5–8) respectively on a Coomassie gel (upper panel) and a Western blot (lanes 9–16 lower panel) of the Coomassie gel probed with the anti-FLAG, M2 antibody (IBI, New Haven, Conn.) followed by goat anti-mouse horse radish peroxidase conjugate (Sigma) as the second antibody and detected by enhanced chemiluminescence (Amersham).

FIG. 8 shows a summary of observed scFv NC10 associations and activity to its target antigen.

Figure 9A:
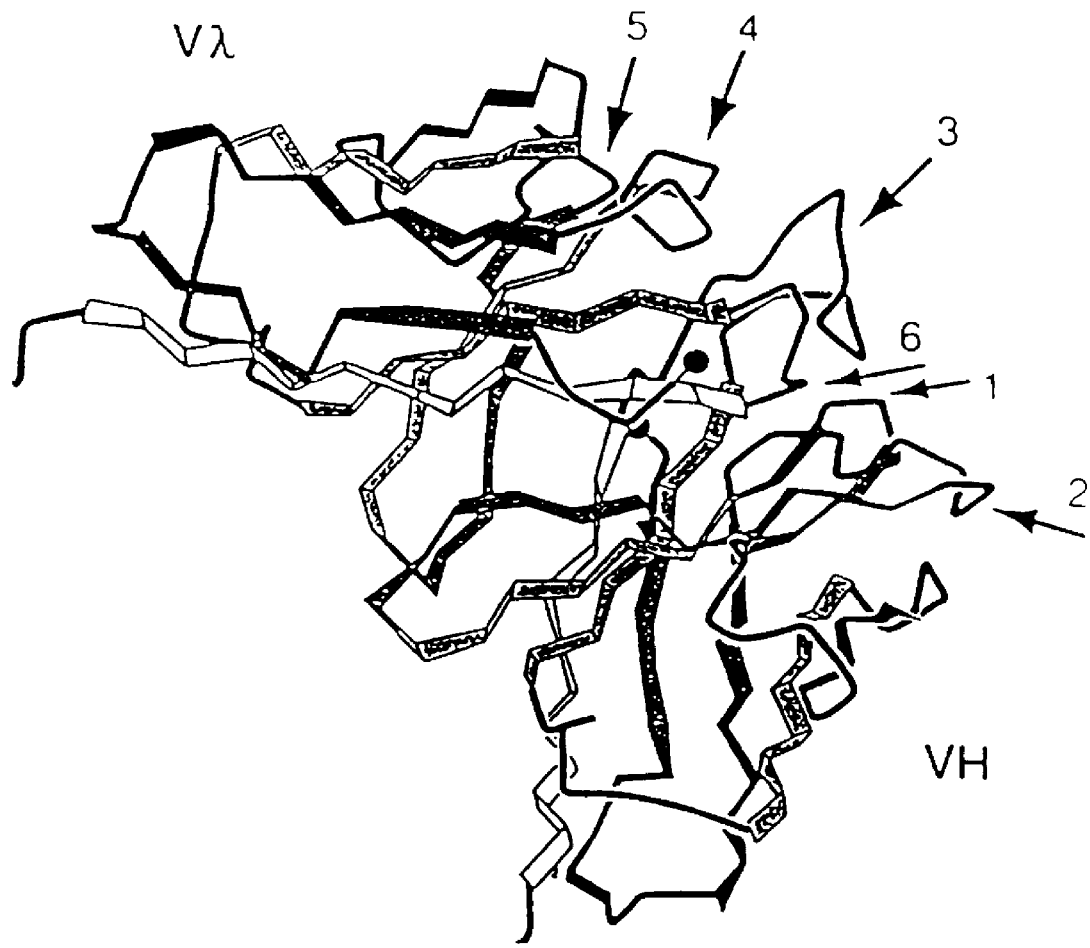
Figure 9B:
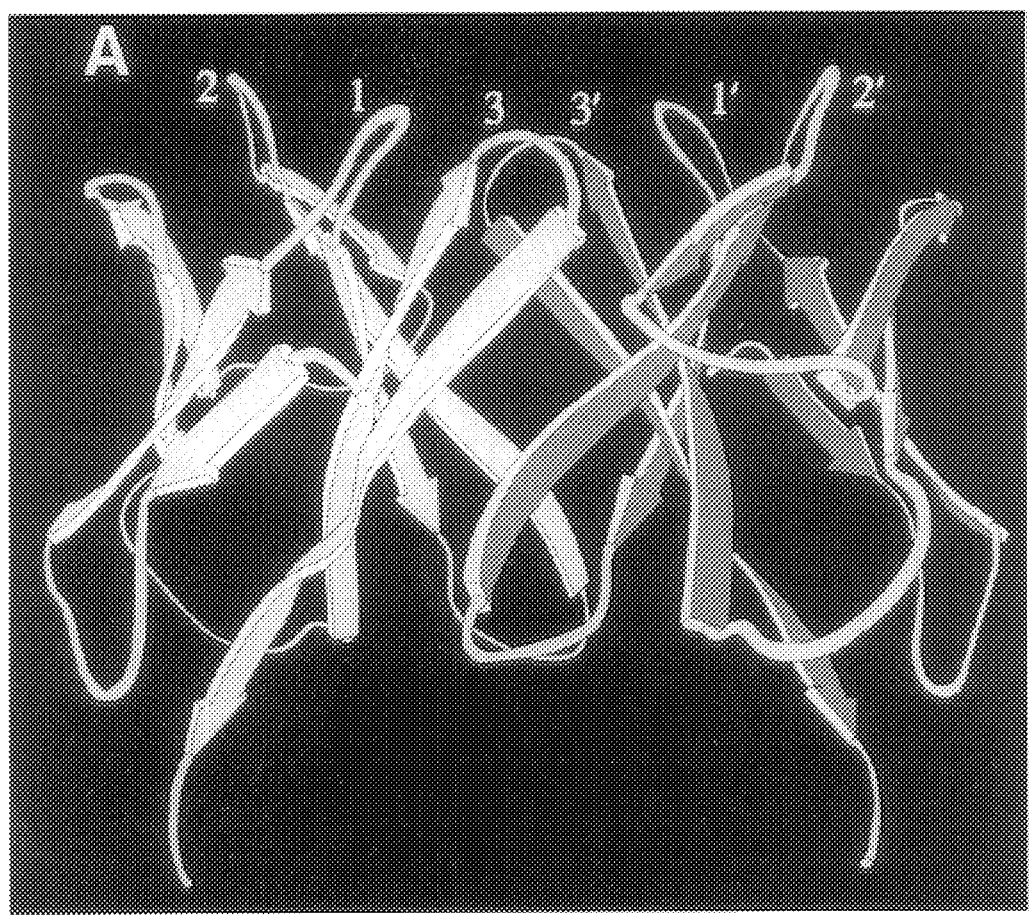

FIG. 9 shows the similarity in structure between an antibody Fv fragment and a CD8 α chain heterodimer.
   a) This is a ribbon drawing of a $V_H$ or $V_L$ molecule showing the CDR loops numbered 1–6 and the structurally conserved framework regions as ribbons.
   b) This is a ribbon drawing of two CD8 α chains. The regions corresponding to antibody CDR loops are shown at the top of the molecule and numbered.

The homodimer is oriented with the molecular dyad axis situated vertically in the plane of the page. CVR-like loops from the top surface of the molecule as shown, and the CDR 1-like, CDR 2-like and CDR 3-like loops are labelled 1, 2 and 3 respectively for one sub-unit, and 1', 2' and 3' for the other sub-unit. The C-termine extend from the bottom of the molecule. The loops forming the dimer interface are the CDR 3-like loops (top) and C-C' loops (bottom).

Figure 10:
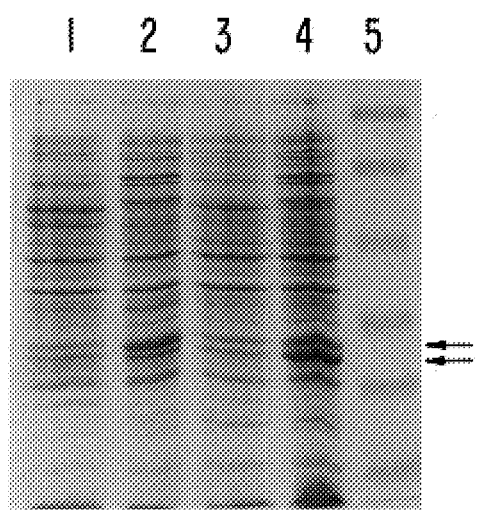

FIG. 10 shows a Coomassie stained SDS-PAGE gel of the synthesised scCD8 in pPOW using *E. coli* host cells pop2136 showing whole cell lysates. Arrows show the positions of the fused and mature (cleared signal sequence) scCD8. In this figure:

Lane 1 uninduced cells containing pPOW-scCD8
Lane 2 4 hours post-induction of pPOW-scCD8
Lane 3 uninduced cells containing pPOW-Lys→Ser scCD8
Lane 4 4 hours post-induction of pPOW-Lys→Ser scCD8
Lane 5 pre-stained molecular weight markers.

Figure 11:
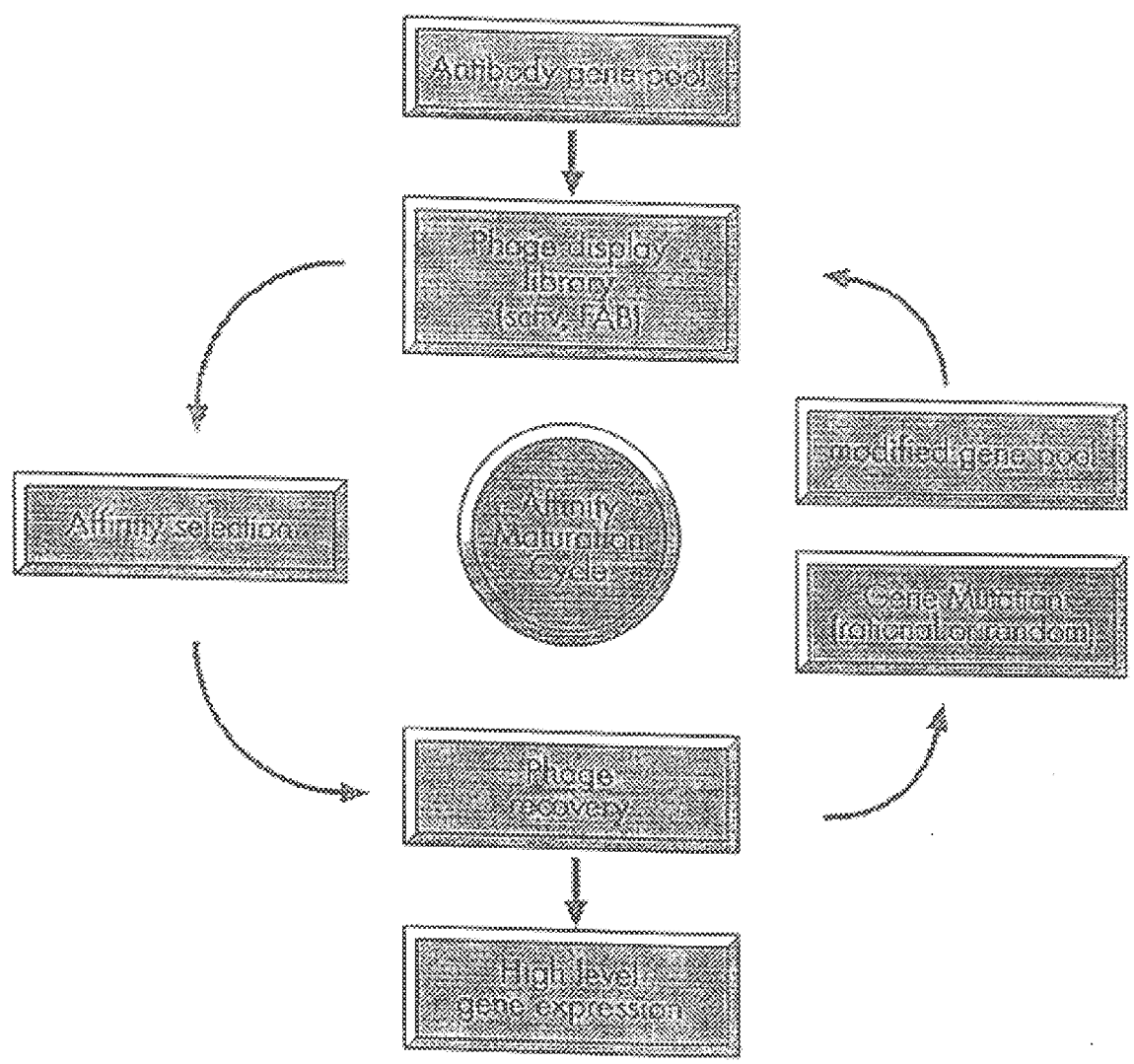

FIG. 11 illustrates a scheme whereby individual antibody genes can be affinity matured. Individual genes can be selected from phage display libraries, and then subjected to rounds of In vivo or in vitro mutations. The affinity matured antibody fragments are then selected for their ability to bind antigen, prior to further rounds of mutation or high level gene expression. Entire antibody libraries can be increased in complexity by cyclic rounds of mutation prior to selection of individual-phage via panning or affinity selection.

Figure 12:
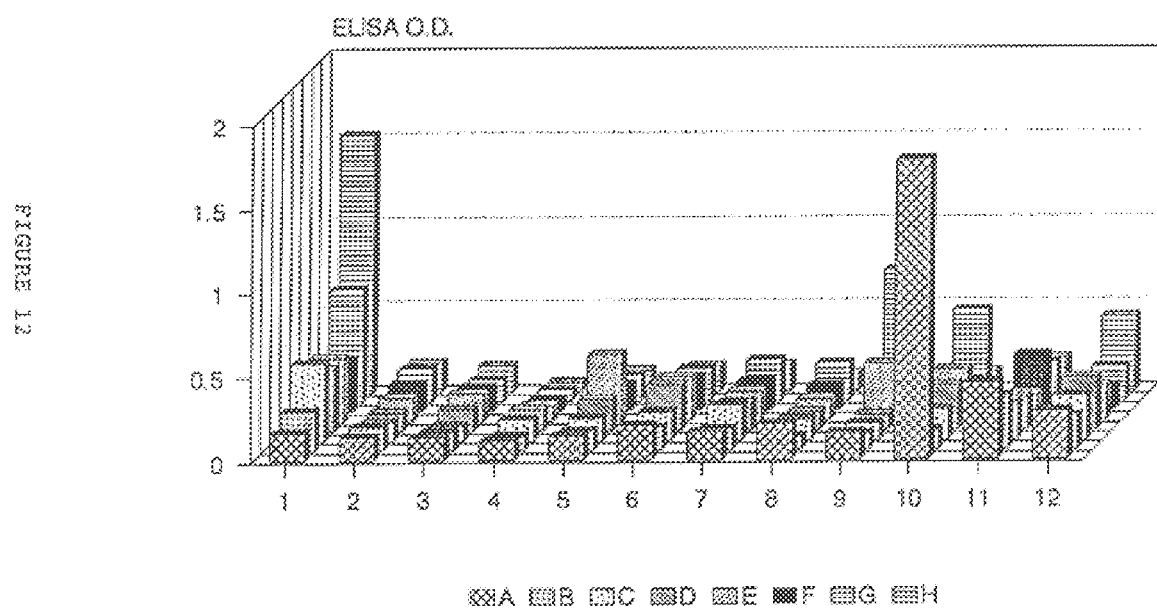

FIG. 12 shows results of ELISA screening of colonies subjected to mutation for affinity maturation.

Figure 13:
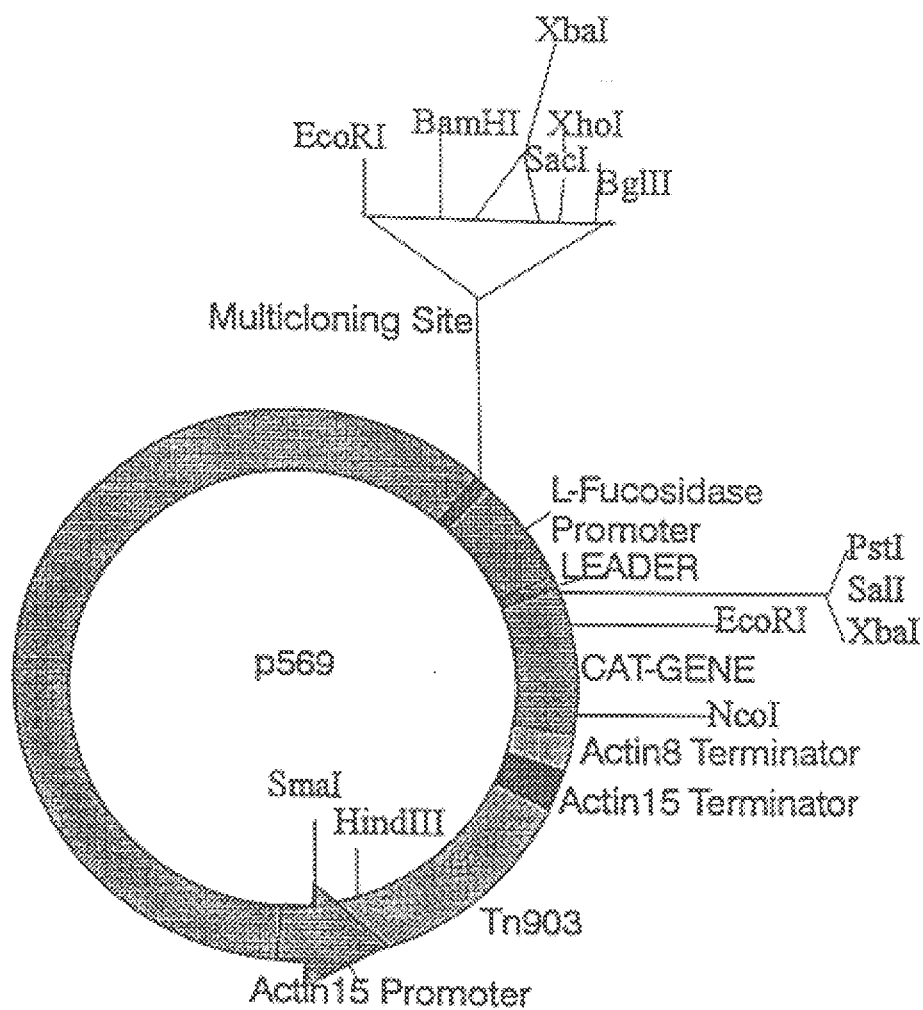

FIG. 13 shows an example of the p569 vector (a gift from W. Nellen), a shuttle vector for expression in D. discoideum. The vector has the alpha L fucosidase promoter and signal sequence, a multi-cloning site, a transcription terminator and the transposon Tn903 for selection by G418.

Figure 14:
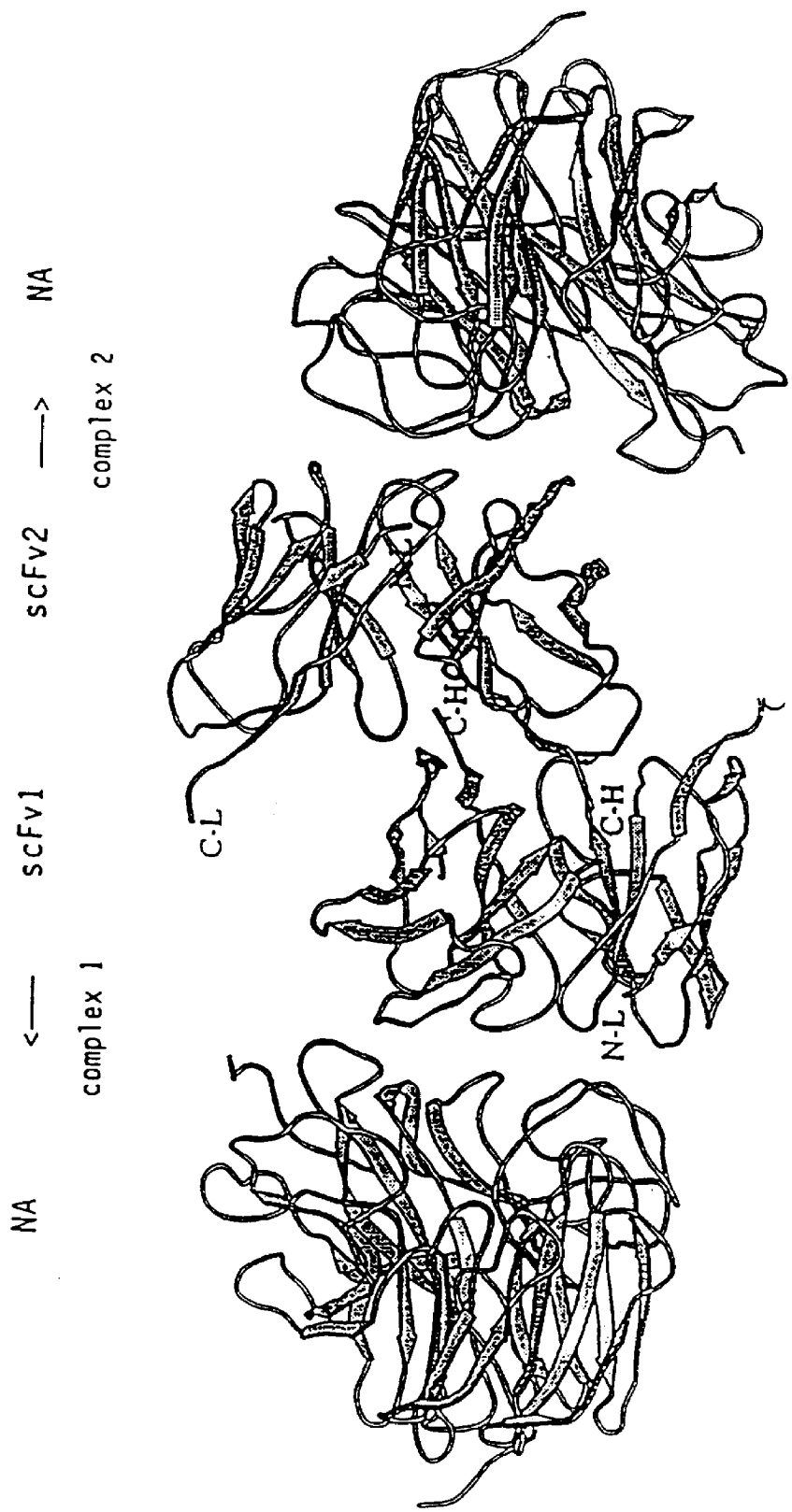

FIG. 14 shows the tertiary structure depicted as the polypeptide backbone of NC10 scFv fragments complexed with two influenza neuraminidase subunits solved at 3 Angstroms resolution by X-ray diffraction analysis. The linker polypeptide joining the heavy and light chain variable regions is not depicted in this figure. In the crystal structure two Fv fragments are associated back-to-back to dimerise two different neuraminidase subunits. In the context of the scFv fragments the dimeric Fv module can be considered a bifunctional reagent.

Figure 15:
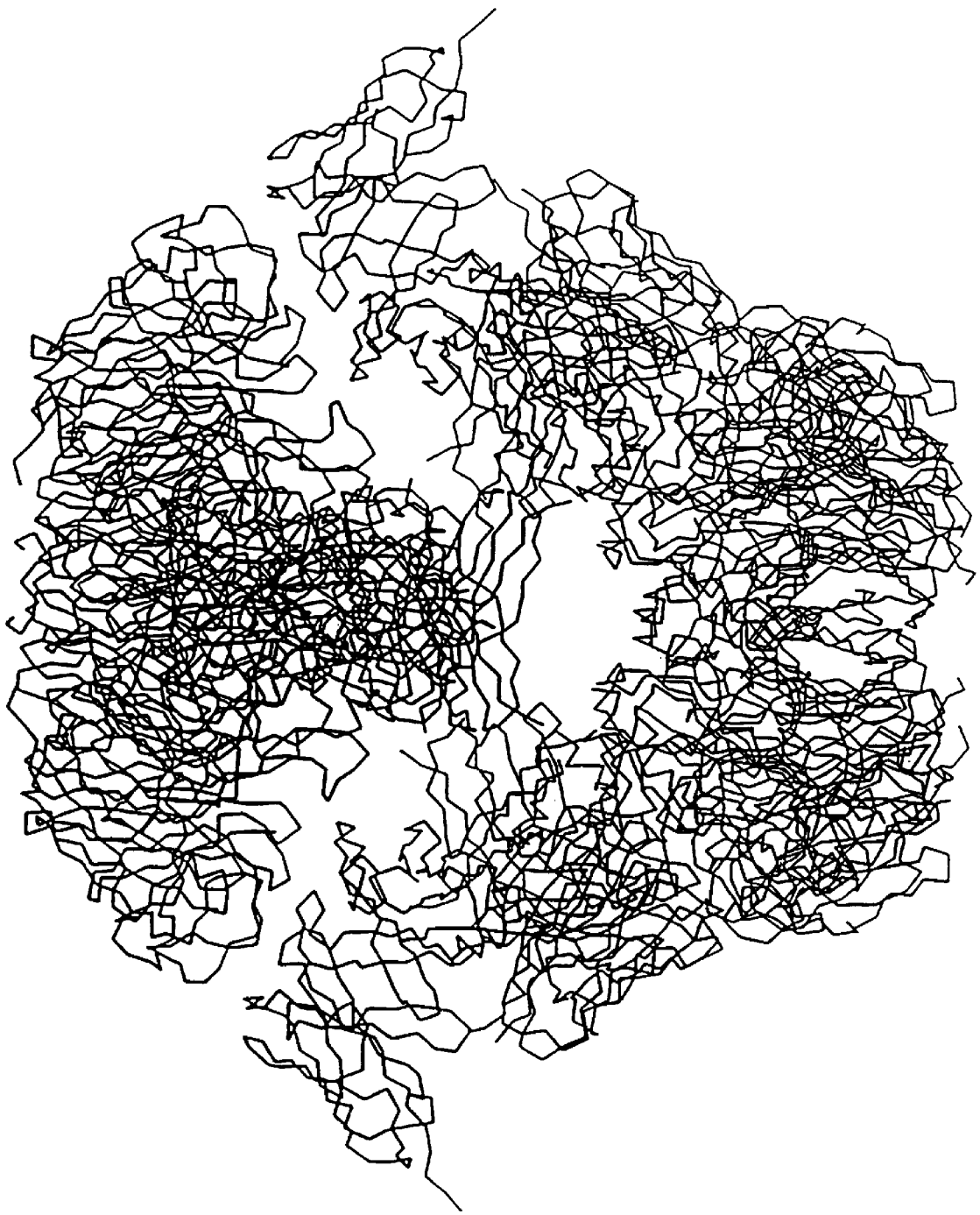

FIG. 15 shows a model of two neuraminidase tetramers which are bound together by four NC10 scFv dimers in solution as resolved by electron microscopy.

Figure 16:
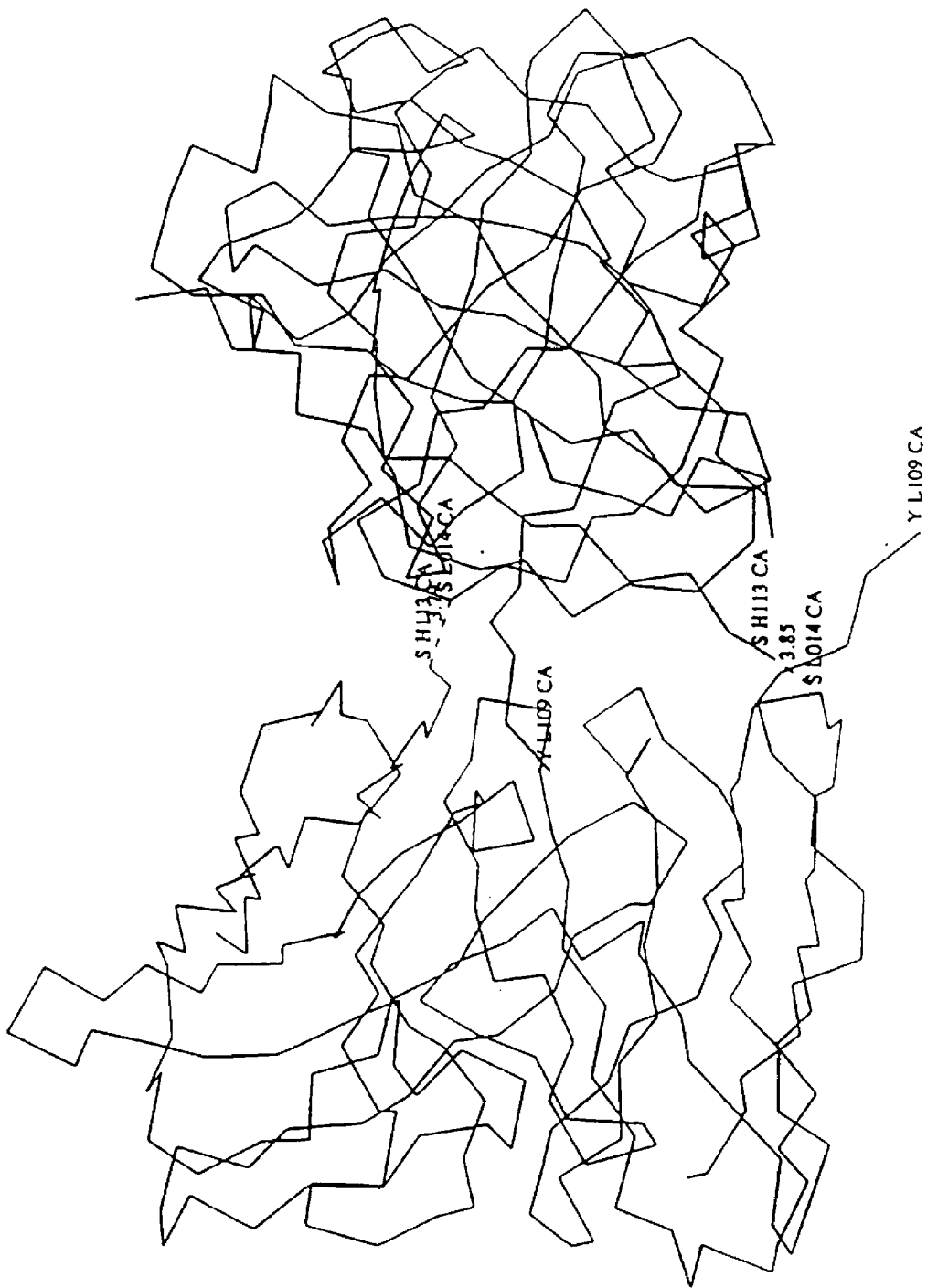

FIG. 16 shows a model of bifunctional Fv molecules dimerised back-to-back and are closely associated without steric interference. In this model, the C-terminus of the heavy chain can be directly linked to the −13 residue of the light chain variable region with minimum reorganisation of the remaining polypeptide backbone.

FIG. 17 shows a schematic representation of non-covalently and covalently joined scFv dimers respectively.

(SEQ. ID NOS: 10 and 9, respectively) shows an example of a mouse Ly-2+Ly-3V domains construct designed for bacterial expression.

(SEQ. ID NOS: 12 and 11, respectively) shows an example of a human single-chain CD8 construct designed for expression in a bacterial secretion vector such as pPOW.

(SEQ. ID NOS: 14 and 13, respectively) shows an example of a mouse MHC α3 domain designed for expression.

(SEQ. ID NOS: 16 and 15, respectively) shows the DNA sequence of the linkerless 1C3 scFv in pHFA.

(SEQ. ID NOS: 18 and 17, respectively) shows the DNA sequence of the anti influenza NC10 scFv with the pel B secretion signal and the FLAG C-terminal peptide.

(SEQ. ID NOS: 19 shows the DNA sequence of the first 1443 bases of the anti-glycophorin 1C3Fab fragment in pHFA ready for ligation post PCR amplification for ligation into p569.

Preferred embodiments of the invention include the following:

1. The structure of the target binding polypeptides may be based on scFv molecules in which one TBR is formed by six surface polypeptide loops to provide contact region to antigen, and hence specificity. In a particularly preferred embodiment, the TBR may be formed by four CDR loops for contact with antigen to provide sufficient contact area and affinity (FIG. 14). Our results using NC10 indicate that it is feasible to randomly mutate these polypeptide sequences to modify target affinity.

2. Bifunctional or polyfunctional reagents can be produced by covalent linkage of individual target binding polypeptides. The covalent linkage can be provided by polypeptide chains in the manner of single-chain Fv molecules. Specificities can be linked by joining together individual proteins, regions which have a propensity for dimerisation or aggregation. Thus it is not necessary for example to link two single-chain Fv fragments in their normal orientation by an additional polypeptide chain, but this can be achieved by linking Heavy and Light chains of differing specificity, or Heavy to Heavy chains, Light to Light chains which can then associate to form functional dimers or aggregates. Of course the method can also be used to join V domains with required specificity to other protein domains, including the Immmoglobulin-like domains derived from CD8, T-cell receptor fragments, or MHC fragments.

In a preferred embodiment the covalent joining of two Ig-like domains, such as the heavy and light antibody variable regions, can be produced with or without a linker polypeptide. For monomeric scFv fragments the polypeptide linker covalently joins the $V_H$ and $V_L$ domains between the carboxyl terminal of one variable (V) domain to the amino terminal of the other V domain without compromising the fidelity of the scFv binding site. The scFv may be assembled in either domain order as a $V_H$-linker-$V_L$ fusion protein or as a $V_L$-linker-$V_H$ fusion protein. The linker should preferably be hydrophilic in nature to prevent it from associating with hydrophobic V domain surfaces. The lengths of the linker may be less than 25 amino acid residues with a preferred size established by empirical selection. A preferred linker sequence consists of pentameric units of Gly4Ser in which the serine residues enhance the hydrophilic characteristics of the peptide backbone, while the glycyl residues give the linker enough flexibility to adopt a range of conformations around the V domains. In a special preferred embodiment the covalent association of polymeric Fv fragments can be produced without an additional linker polypeptide by removal of a segment of one Ig-domain at the junction sequence. These linker-minus constructs are referred to herein as tightly coupled domains (TCDs). The number of amino acids to be removed can be determined either empirically or with the aid of protein design considerations. FIG. 16 depicts is the association of two Fv molecules "back-to-back" as TCDs and in which the two TBRs are at opposite ends of the molecule thus forming a bifunctional reagent capable of cross-linking two target molecules. In this example, preferably up to 13 amino acids are removed for close association. The resultant molecule has a propensity for oligermerisation, at least to dimers, with a close but not sterically inhibited interaction between the Ig-like domains. It will be appreciated that polypeptail tails can be added at the free amino and carboxyl terminii to increase the number of TBRs on the molecule. It will also be obvious that the missing polypeptide sequences that had been removed at the junction of Ig-like domains can be replaced, in whole or in part, by providing the polypeptide sequences attached to another position in the Ig-like domains. We anticipate that these molecules will be capable of forming two-dimensional arrays thereby providing a bifunctional surface. It will be appreciated that these arrays will have special application as biological coating devices.

3. The complete three-dimensional structure of mature human or mouse CD8, comprising heterodimeric α and β chains, is not yet known. Predictions from a crystal structure of homodimeric human CD8α suggests that the α chains are similar in topology to antibody $V_L$ domains (Leahy et al, Cell, 1992 68 1145–1162). We have constructed single-chain variants of mouse CD8α/β heterodimer for expression using bacterial secretion vectors, and similar results would be expected using human CD8. Native human or mouse CD8 molecules are presumed to have affinity only for MHC Class I molecules. We predict that random library approaches, such as those described in the Examples herein, will enable scCD8 molecules to be used as a stable framework for the production of target binding polypeptides. By this process, scCD8 molecules can be used as antibody mimics. Furthermore, the scCD8 molecules can be further modified in the size and conformation of CDR-equivalent loop structure to provide a framework for less than six CDR loops in the contact surface. In a particularly preferred embodiment, we envisage a stable protein framework capable of providing four or five CDR loops in the contact region. We also envisage the strategy to apply to other Ig domains. For example the immunoglobulin-like domains of MHC Class I and II can be expressed in soluble form and when modified can be used as immunomodulatory reagents.

Figure 1:
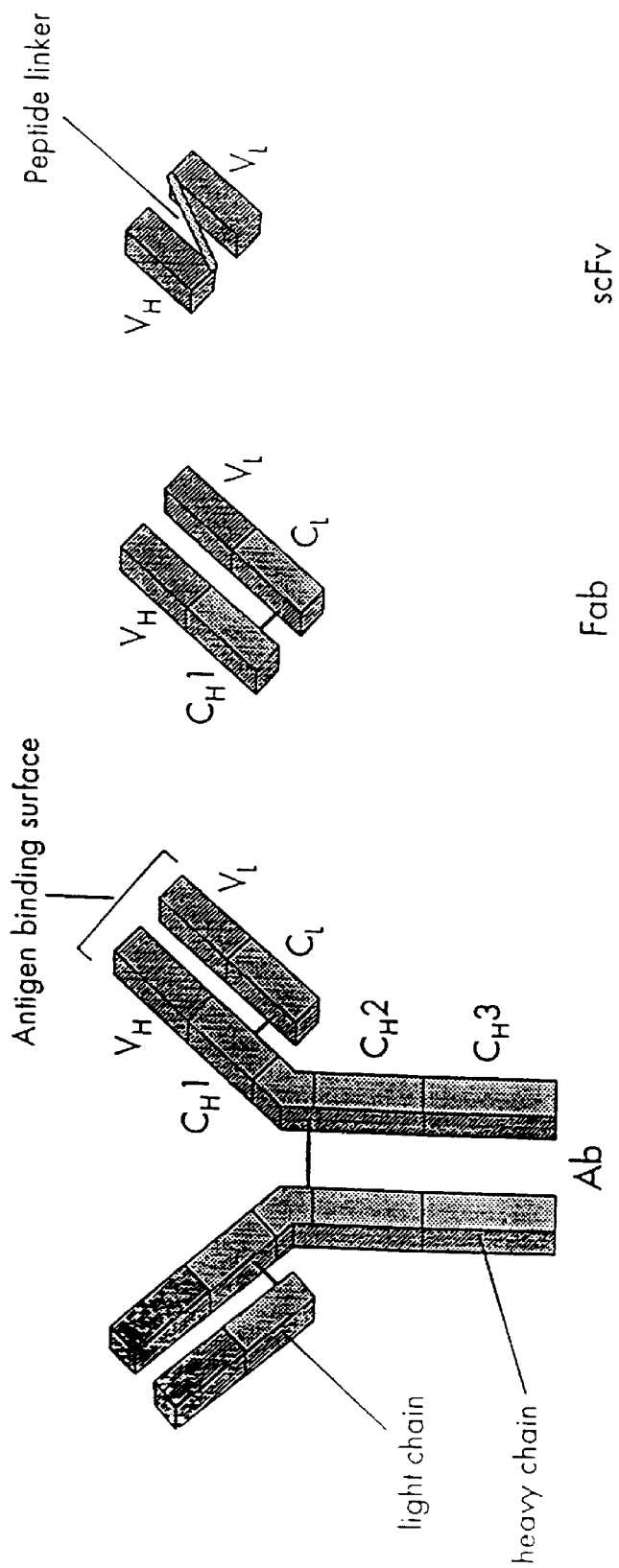
Figure 2:
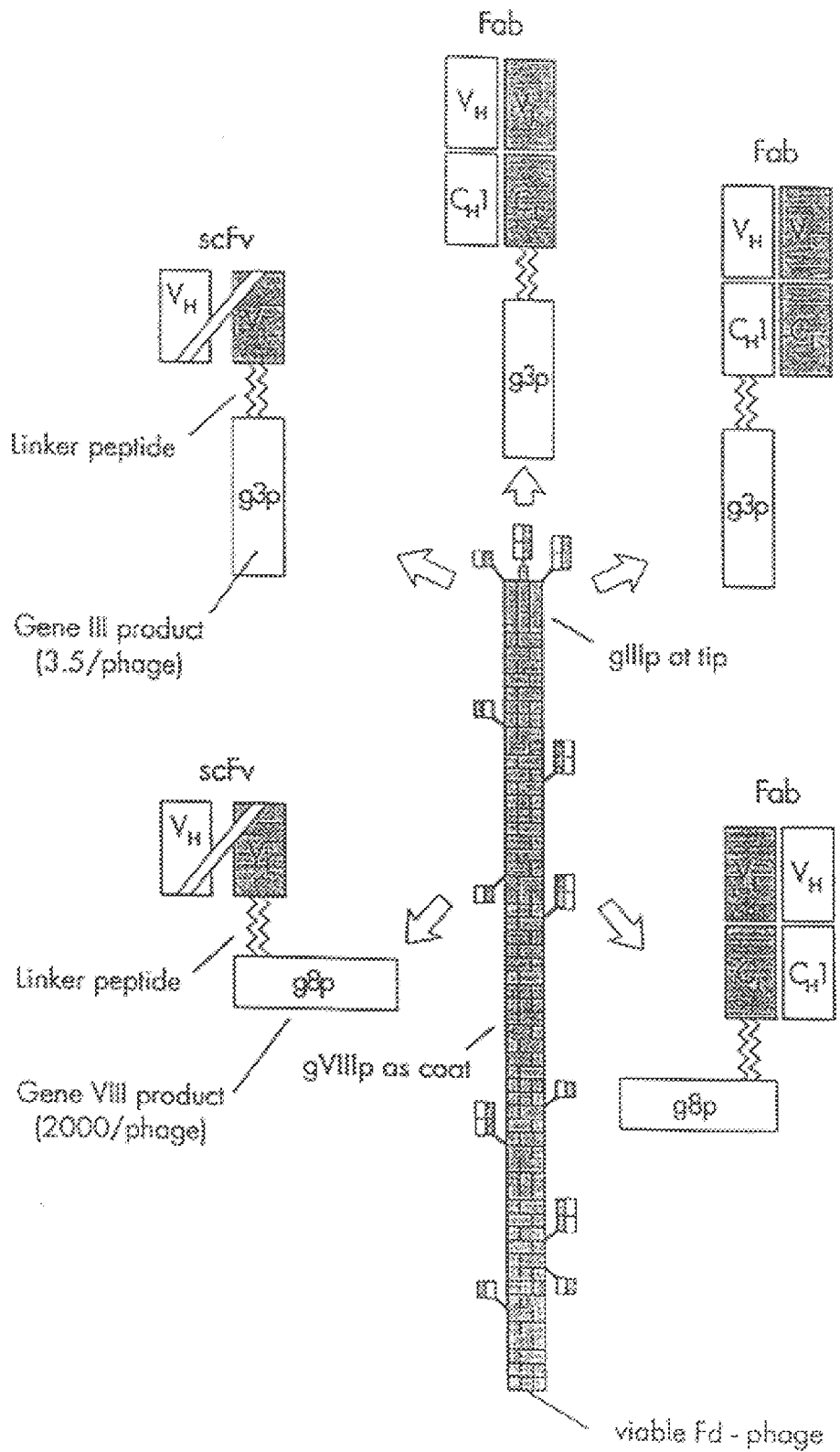
Figure 3:
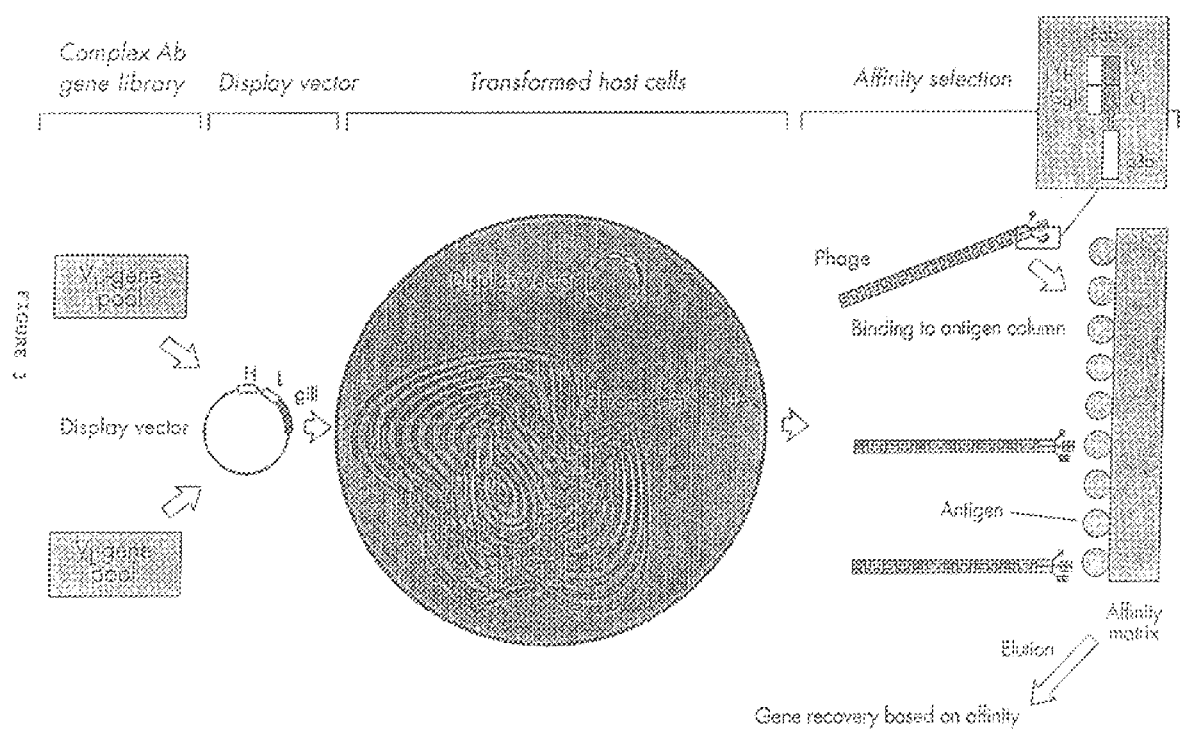
Figure 4:
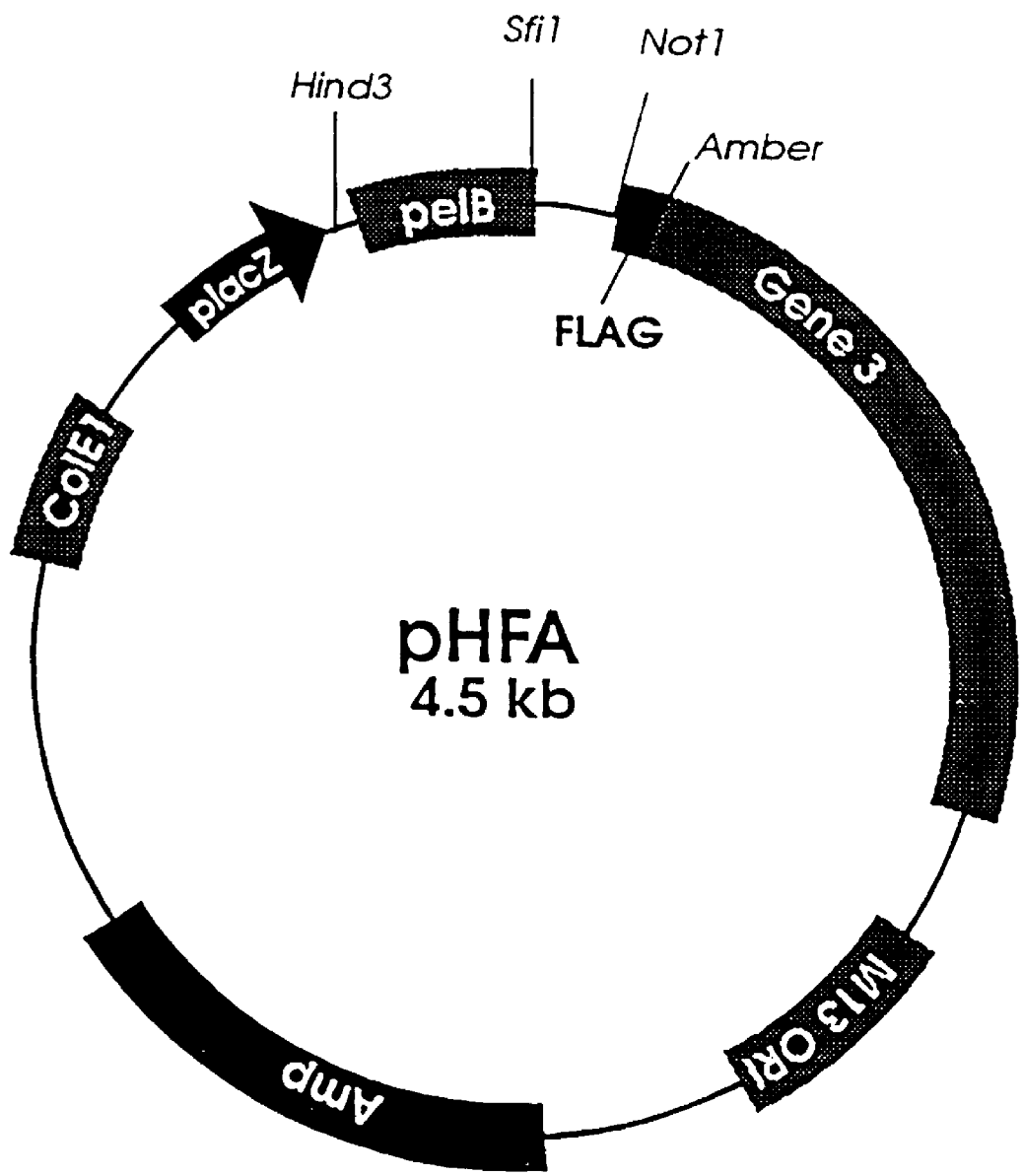

4. Modifications to target binding polypeptides such as those described above can be based on mutation of the coding region, by the use of library selection and modification strategies such as those shown in FIG. 3, to mature a single TBP or TBP library of low affinity and wide specificity to enhance the range of target molecules which it recognises, but more importantly to produce a range of binding affinities for each member of the library, the individual DNA coding regions of which may be easily selected and isolated by modifications of known methodologies. It is envisaged that such a library will comprise antibody-like fragments, or any other peptide which shows an affinity for a ligand or another protein, enzyme or receptor. This may also include a stable core polypeptide which is not in itself antigenic, but may be modified by the addition of CDR loops or peptides with an affinity for specified ligands by grafting the coding regions by recombinant DNA techniques. It can also be seen that a change or changes to the framework regions may result in a change of conformation of the protein such that an altered binding surface is presented, with binding properties different from those of the parent molecule.

The most trivial example includes the construction of expression libraries that produce recombinant antibody fragments (including single-chain Fv fragments) with predetermined target binding specificity. In vitro mutation and affinity maturation provide means of presenting the binding molecule such that the appropriate coding regions are selected and retained. Presentation vectors which will allow continual-reassortment of the binding domains (which in this example as a preferred embodiment will encompass $V_H$ and $V_L$ domains) subsequent to each of the selection steps shown in FIG. 3 can suitably be used, for example pHFA.

5. The invention may be used for the construction and selection of a wide range of receptors, receptor-like molecules and molecules constructed with mutations in potentially critical regions for both binding, structural integrity and biological activity. Initially phage surface presentation after expression and phage rescue from *E. coli* is used to monitor the efficacy of this approach, but other systems such as the eukaryotic systems are also expression competent. Yeast (*Saccharomyces cerevisiae*) has been shown to express the $V_H$ of NC41, a monoclonal antibody directed against influenza virus neuraminidase, under the control of the alpha mating factor promoter, and the slime mould *Dictyostelium discoideum* is able to express recombinant proteins including both $V_H$ and the scFv of NC10.

Figure 5:
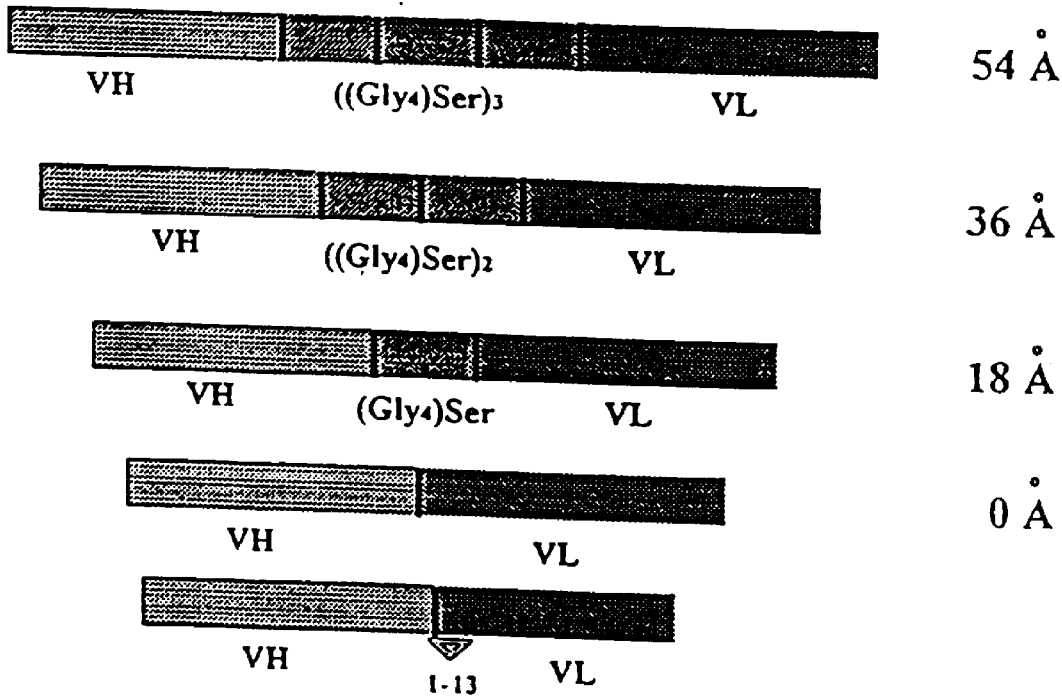
FIG. 5 shows the series of scFv NC10 deletion linker constructs and the theoretical minimum distance (in Angstroms) spanned by the polypeptide linker.

6. The specific selection of target-binding polypeptides able to bind to the specified antigens (which may include LIF, TGF-α, glycophorin, cell surface markers or other cell specific surface proteins), is made possible as a result of the presentation on the display vector, for example the presentation on the phage surface of these peptides fused to the Gene III product. Having selected the appropriate phages, they are then subjected to rounds of mutation, as shown in FIG. 5.

In the following examples, the mutD and mutT1 mutator strains of *E. coli* are used to induce mutations at random throughout the molecule. This is done by transformation of these *E. coli* strains with the plasmid DNA by any of the standard techniques that appear in the literature; the preferred method is by electroporation. Alternatively the recombinant phage may be transfected into the mutator strains by standard transfection methods. After rounds of growth of these plasmid/phage-bearing *E. coli,* the phage may be rescued by standard techniques with a helper phage, and can then be used in antigen-binding assays to determine the effects of various mutations on the binding affinity.

These mutations are not confined to base substitutions in the DNA, but may also encompass the addition of peptides to the structure of the molecule such that the number, size and location of the binding regions in the molecule is altered. A single domain binding unit with these additions will show binding characteristics of substantially altered affinity if not specificity. The correlation between mutation at specified sites and the binding affinity may then be used to design novel CDR loops and framework regions for target binding polypeptides with therapeutic and diagnostic potential.

Also included in the scope of the invention is the expression of recombinant proteins from recombinant cells under the direct control of the antigen, or some other ligand which is responsible for the first step in the process towards controlled expression of the "antibody genes".

7. Bifunctional or polyfunctional reagents can be selected using the library technology described above. Target binding polypeptides may be displayed for affinity selection by attachment through a polypeptide tail. Selection based on affinity to two or more different target antigens or haptens will select a single molecule which has two binding surfaces at different positions of the same molecule. The binding surfaces can be overlapping. To construct a library for selection of bifunctional or polyfunctional reagents, the strategy of site specific and random mutagenesis applied to two or more surfaces of the protein molecules may be used. In the case of single-chain Fv or CD8, the preferred regions for mutation will be the CDR loops and their opposite counterpart loops at the other end of the scFv molecule. In the case of Fab molecules, the preferred mutations will be at CDR loops and the opposite counterpart loops at the other end of the constant domains.

Unless otherwise specifically stated, all standard methods referred to herein are to be found in "Molecular Cloning-A Laboratory Manual" Sambrook et al 1990.

EXAMPLE 1

Construction and Expression of Target Binding Polypeptides as Single Chain Fv Fragments Using Polypeptide Linkers of Different Lengths A parent scFv fragment of NC10 (a monoclonal antibody that recognises the neuraminidase (NA) molecule on the N9 strain of influenza virus) was designed, constructed and expressed in *E. coli* (Sequence I.D. 5). The amino terminal secretion signal PelB directed the synthesised protein into the *E. coli* periplasm where it became associated with the insoluble membrane fraction. An octapeptide (FLAG; IBI USA) tail was fused to the carboxyl-terminal of the scFv and was used to monitor the scFv through subsequent purification procedures. This reagent is bifunctional with specificity to both neuraminidase and anti-FLAG antibodies.

The scFv NC10 protein was purified by solubilization of the *E. coli* membrane fraction with guanidinium hydrochloride followed by column chromatography. Size exclusion HPLC of purified scFv NC10 showed that the scFv fragment emerged in two peaks corresponding in size to monomers (27 kDa) and dimers (54 kDa). Furthermore, the monomeric form bound to N9 NA to form a complex of ~320 kDa while the dimeric form bound to N9 NA to form a complex of ~640 kDa. The 320 kDa complex could consist of four scFv molecules binding to a single NA molecule, while the 640 kDa complex could consist of four scFv molecules binding to two NA molecules. Electron microscopy confirmed the tight coupling of two neuraminidase tetramers by four bifunctional scFv dimers (FIG. 15). High resolution electron microscopy was performed on the tern N9 (avian) strain of influenza neuraminidase complexed with scFv constructs of the NC10 of the Mab, where the molecular complexes were stained (contrasted) either with potassium phosphotungstate at pH 7.0 or with uranyl acetate at pH 4.0.

Based on our previous extensive experience of imaging molecular complexes of the same N9NA with monoclonal Fabs (32/3, NC35 and NC41) and with whole monoclonal IgGs (32/3, NC41 and NC10), we were able to interpret the N9Na-scFv complex images as closed structures of pairs of neuraminidase heads coupled together face-to-face by four bridging scFv dimers in such a manner as to maintain four-fold point-group symmetry of this densely packed molecular complex (FIG. 15). This image interpretation of the N9Na-scFv molecular complex is directly compatible with the observed molecular weight of the complex in solution of $M_r$~610,000.

X-ray diffraction analysis of crystals in which the scFv is complexed with neuraminidase (FIG. 14) demonstrates a close association between two scFv molecules related by a two-fold axis of rotation. Two possible dimeric conformations are possible. In the first instance the $V_H$ and $V_L$ domains encoded by a single polypeptide chain with additional peptide tails form a bifunctional scFv which associates non-covalently with the separate scFv molecule (FIG. 17). In the second instance, the $V_H$ and $V_L$ domains forming the antigen binding surface (the TBR) in each Fv are non-covalently associated and the two Fvs are covalently joined by the linker polypeptide (FIG. 17).

Molecular modelling studies (FIG. 14) indicate the distance between the $V_H$ and $V_L$ domains of a non-covalently associated dimer would be at least 35 Å, whereas the distance between the $V_H$ and $V_L$ domains of a covalent dimer would be less than 25 Å. Given the 3.8 Å (0.38 nm) distance between adjacent peptide bonds and the distance lengths that the linkers can theoretically span (54 Å, 36 Å, 18 Å and 0 Å for the 15, 10, 5 and 0 residue linker pPOW-scFv NC10 constructs respectively) we examined the type of scFv-NA complexes formed when scFv proteins with different linker lengths bind to antigen.

A series of scFv NC10 proteins with shortened linker lengths were constructed (FIG. 5). The first pPOW-scFv NC10 construct has a polypeptide linker consisting of three pentameric Gly4Ser units (this pPOW-scFv NC10 construct was referred to as the 15 residue linker, $V_H.15.V_L$). The deletion linker mutants were constructed by sequentially removing each of these pentameric units to form constructs with two, one and zero units (referred to as the $V_H.10$, $V_L$, $V_H.5.V_L$ and $V_H.V_L$ residue linker pPOW-scFv NC10 constructs respectively). Furthermore, a scFv NC10 construct was made by deleting the first β-strand of the $V_L$ domain (the first 13 amino acids) so that the carboxyl-terminal of the $V_H$ domain joined directly to the $V_L$ domain ($V_H.-13.V_L$).

Detailed Construction of pPOW-scFv NC10 with Shortened Linker Lengths

The pPOW-scFv NC10 construct was digested successively with BstE II (New England Biolabs) and Sac I (Pharmacia) according to manufacturers' specifications and the polypeptide linker released. The restricted linkerless pPOW-scFv NC10 DNA was electroeluted from an 0.8% agarose gel and the DNA concentrated by precipitation with 0.3M Na acetate and 2.5 volumes of ethanol. Synthetic oligonucleotides were phosphorylated at their 5' termini by incubating at 37° C. for 30 min with 0.5 units of T4 polynucleotide kinase (Pharmacia) and 1 mM ATP in One-Phor-All Buffer PLUS (Pharmacia). Pairs of complementary phosphorylated oligonucleotide primers (FIG. 6) were premixed in equimolar ratios to form DNA duplexes encoding single chain linkers of altered lengths. These duplexes were ligated into the BstE II-Sac I restricted pPOW-scFv NC10 plasmid using an Amersham ligation kit. A slightly different approach was required to make the $V_H.-13.V_L$ construct. An oligonucleotide primer (FIG. 6) spanning the deleted $V_L$ domain was constructed and used in conjunction with a FLAG specific oligonucleotide (FIG. 6) to amplify by PCR a $V_H$–13.$V_L$ fragment of the scFv NC10. The amplification product was digested with BstE II and EcoR I and ligated into similarly digested pPOW-scFv NC10 plasmid using an Amersham ligation kit. The ligation mixtures were purified by extraction with an equal volume of phenol/chloroform and precipitated with 0.3M Na acetate and 2.5 volumes of ethanol. The ligated DNA was resuspended in 20 ml H20 and 5 ml of the sample was transformed into E. coli DH5a (supE44, hsdR17, recA1, endA1, gyrA96. thi-1, relA1) and LE392 (supE44, supF58, hsdR14, lacy1, galK2, galT22, metB1, txpR55). Cells were shaken in 1 ml of LB medium for 1 hr and plated onto 2xYT medium with 100 mg/ml ampicillin. Recombinant clones were identified by PCR screening with oligonucleotides directed to the PelB leader and FLAG sequences of the pPOW vector. The DNA sequence of the shortened linker regions were verified by sequencing double-stranded DNA using Sequenase 2.0 (United States Biochemical).

Protein Expression of the scFv NC10 Proteins with Shortened Linkers

Transformed LE392 were grown overnight at 30° C. in SB medium and diluted 1:10 to inoculate fresh SB-medium. Cultures were grown at 30° C. with shaking until the absorbance at 600 nm ($A_{600}$) was approximately four. The temperature was raised to 42° C. for the-remainder of the induction period (which continued for 4 hr until the-$A_{600}$~7). Cells were recovered by centrifugation (Beckman JA10 6,000 rpm for 15 min) and the supernatant fraction removed. The cell pellet was resuspended in 10% of the original volume in 20% sucrose, 10 mM Tris.HCl. pH7.5 and left on ice for 5 min. EDTA was added to a final volume of 5 mM and the mixture incubated on ice for a further 10 min and centrifuged as before to pellet the cells. The supernatant was discarded and the cell pellet resuspended in $H_2O$, the mixture was recentrifuged and the supernatant containing the periplasmic proteins removed. The resulting cell pellet was resuspended in $H_2O$ and lysed by sonication (six 30 sec bursts-for large scale preparations and one 30 sec burst for small scale preparations) and kept on ice for 5 min. After centrifugation the aqueous phase was recovered as the solubilized cytoplasmic fraction while the pellet contained the insoluble membrane-associated fraction. To verify scFv NC10 expression total cell lysate from individual clones were analysed by SDS-PAGE under reducing conditions and Western blotting using the anti-FLAG monoclonal antibody, M2 (FIG. 7). Single positive bands migrating at ~28, 29, 31 and 32 kDa were observed (FIG. 7, lanes 13–16) which correlate with the anticipated Mr of the scFv NC10-FLAG fusion protein synthesised by pPOW-scFv NC10 constructs with 0, 5, 10 and 15 residue linkers respectively. ScFv NC10 proteins with 0, 5, and 10 residue linkers showed the same characteristics as the 15 residue linker. The scFv NC10-FLAG fusion proteins were associated with the insoluble membrane fraction of E. coli, approximately half of which could be solubilized by treating with guanidinium hydrochloride.

The soluble products were purified by gel filtration and chromatography on Mono-Q or on an affinity matrix containing an antibody specific for the tail moiety. The pure products were characterized by SDS-PAGE, size exclusion HPLC (SE-HPLC), ultracentrifugal analysis, binding activity towards-the parent antigen (influenza virus neuraminidase), electron microscopy of the complexes formed between the antigen and reagent. Cross linking experiments confirmed the size of the products. The properties are summarized in FIG. 8.

EXAMPLE 2

Construction of mouse and human scCD8

The α and β chains containing only the V-like domains of mouse CD8 were amplified separately by PCR with Vent polymerase using primers containing homology to the V-like domains (using available database sequences) and with additional nucleotides encoding the $(Gly_4Ser)_3$ linker (Sequence I.D. 1). After annealing the two separate domains the products were extended using dNTPs and polymerase. The scCD8 gene was amplified using new primers containing MscI site at the 3' end and SalI site at the 5' end. The single chain product was digested with MscI and SalI then cloned into MscI and SalI digested pPOW vector. High level protein synthesis was obtained in E. coli host cell strain pop2136. An N-terminal modification was designed to increase the synthesis of correctly cleaved product which was achieved by changing the N-terminal residue of mouse CD8 α chain from Lysine to Serine (the Human CD8 a chain N-terminal residue is a Serine). The synthesis of scCD8 in pPOW using E. coli host cell strain pop2136, showing whole cell lysates, can be seen in FIG. 10. The synthesised scCD8 product was detected by anti-CD8 antibodies that only recognise protein in the conformationally correct form.

Human scCD8

The DNA encoding the V-like domain of the mature α chain protein was amplified by PCR using Taq polymerase and primers containing homology to the V-like domain (using available database sequences) with additional nucleotides encoding the $(Gly_4Ser)_3$ linker and incorporating restriction enzyme sites MscI and BamHI (Sequence I.D. 2). The V-like domain of the CD8 β chain was amplified by PCR directly from DNA isolated from blood using primers containing BamHI and EcoRI restriction enzyme sites. The two individual products were digested with the appropriate enzymes then ligated into MscI and EcoRI digested pPOW vector.

The DNA sequence of each of the single chain CD8 constructs was confirmed by double stranded DNA sequencing. The nucleotide sequence can be seen in Sequence I.D. 1 and 2. In this example the vector directs the synthesis of a scCD8 with a C-terminal peptide tail for diagnostic and coupling applications, including affinity purification.

Preferred techniques to monitor the biological activity of the scCD8 product include:

a) Direct measurement of protein binding affinity for example using biosensor technology or ultracentrifugation using binding to whole cells, cell surface molecules or their fragments such as β2 microglobulin or the α3 domains of the MHC class I molecule.

b) measurement of binding to the MHC class I molecules expressed in RMA-S cells (peptide loaded) using the C-terminal peptide tails as diagnostic markers.

c) an interference of function assay such as monitoring changes to the peptide induced dose-dependent effect on IL2 production during T-cell activation.

EXAMPLE 3

Construction of Linkerless AntiGlycophorin 1C3

The parent IC3 antibody and scFv derivatives are disclosed in the International Patent Application No. PCT/AU93/00228.

Oligonucleotide N2034 (SEQ ID NO: 1) (5'-ACGTAGGTCACCGTCGCCTCCGACATCGTCATGT-CACAGTCTCCATCCTCC-3') was synthesised to have complementarity to the last 15 bases at the 3' end of 1C3 $V_H$ coupled directly to the first 30 bases of the 1C3 $V_L$ 5' sequence without any intervening linker sequence.

Oligonucleotide N2035 (SEQ ID NO: 2) (5'-TTTATAATCTGCGGCCGCCCGATTAATTTC-3') was synthesised to have complementarity to the 1C3 $V_L$ sequence on the opposite strand around the Not I site near the 3' end.

The two oligonucleotides were used with 1C3 template DNA in a Polymerase Chain Reaction to produce a 1C3 product of 3'-$V_H$ sequence juxtaposed to 5'-$V_L$ sequence flanked by Bst EII and Not I restriction endonuclease sites.

After incubation of the PCR product with restriction endonucleases Bst EII and Not I, the resultant fragment was ligated with vector pHFA containing the 1C3 scFv sequence previously digested with Bst EII and Not I to remove the intervening sequence. The ligated product was used to transform E. coli strain TG1. Transformant colonies containing inserts were verified as containing the DNA sequence as shown in Sequence I.D. 4.

This gene construct was expressed in this vector and related vectors when transferred to a non-suppressor E. coli strain and induced with IPTG, or by transferring the 1C3 coding region to the thermoinducible expression vector pPOW.

EXAMPLE 4
Mutation with mutator strains of E. coli

The NC10 scFv plasmid coding for the expression of the recombinant antineuraminidase antibody NC10 scFv was electroporated into E. coli mutD. Mutants were produced by subjecting the samples to the mutation cycle shown in FIG. 11. They were grown for 50 generations in exponential phase (to induce mutation of the phasmid DNA) in YT+AMP+TET and then rescued with the helper phage. The rescued phage was applied to the immunotubes previously coated with 10 μg/ml of the antigen, non-binding phage removed by washing with PBS etc and the specifically bound phage eluted with 100 mM triethylamine, collected into 0.5 volumes of 1M Tris-Hydroxymethylmethylamine-HCl pH 7.5 and then transfected into mutD cells by standard methods, (unless otherwise specifically stated all standard methods referred to herein are to be found in "Molecular Cloning-A Laboratory Manual" Sambrook et al, 1990) and again grown through 50 generations whilst maintaining the cells in the logarithmic phase of growth. After an appropriate number of rounds of mutation selection which in this example is three the phage titres are in the region of $10^7$–$10^8$ phage/ml. After the final panning step, eluted phage were transfected into E. coli TG1 cells and plated onto YT+AMP+ Glucose plates and then each of the isolated colonies grown before phage rescue and analysis by ELISA on "flu" virus or glycophorin. The colonies which exhibited non-wild-type levels of ELISA activity, were then amplified, the DNA sequenced and the phage transfected into E. coli HB2151 cells available from the American Type Culture Collection, for soluble expression. The phage were transfected into HB2151 by the standard methods and the selected individual colonies of each phage sample grown in YT+AMP(100 μg/ml) prior to induction with 1 mM IPTG (isopropylthiogalactoside) for 4 to 16 h at 37° C., with or without subsequent incubation at 4° C. for 16 h. The culture supernatant and the extracts of periplasm, cell membranes and cell cytoplasm were collected and analysed for the recombinant gene expression as described (Power et al, Gene 1992 113 95–99).

EXAMPLE 5

The recombinant 1C3 scFv (a glycophorin-binding antibody coding region) in the phagemid pHFA prepared as described in International Patent Application No. PCT/AU93/00228 was subjected to random mutation in the mutD E. coli as discussed in Example 4, and the selection protocol similarly applied, with the exceptions that the selection involved coating the solid phase matrix (ELISA plate, Immunotube, or latex bead) with glycophorin A from a 10 μg/ml solution in PBS. The results of the ELISA screening for selection of individual colonies is illustrated in FIG. 12. Competitive ELISA assays, using detection with anti-FLAG antibody, were performed on selected colonies after mutation, and Table 1 shows the increases in relative affinity of the expressed proteins for the antigen asialoglycophorin.

TABLE 1

| recombinant cloned scFv | Mutation | Affinity nM (off rate) |
|---|---|---|
| 1c3 | wt | 62 |
| 1c3.A13 |  | 40 |
| 1c3.B7 |  | 29 |

EXAMPLE 6

A scFv library in the phagemid vector pHEN (MedicalResearch Council, U.K.) was transferred into the mutD strains of E. coli and treated as for Examples 4 or 5 for the mutation, detection and selection of scFv with modified binding ability. Selecting for glycophorin binders. To increase the range of glycophorin-binding antibodies available the naive scFv library was used as the starting point for this maturation and affinity selection of phage displayed scFvs. Two of the unique anti-glycophorin scFvs that were selected from the naive scFv phage display library, have the deduced amino acid sequence shown for the region of their Vk4 chains that were subsequently shown to be mutated are shown in Table 2.

TABLE 2

(SEQ ID NOS:3–4)

F T A S T G D V P D R F S G S G S G T D F T L R I S S L Q A E D V A V Y Y C Q Q A S V F P

C I Y W N P D S P D R F S G S G S G T D F T L R I S L Q A E D V A V Y Y C Q Q A S V F P

60

Affinity maturation of each of these molecules was achieved by using the mutation (mut D5) affinity selection cycle, as we show in FIG. 11, and the changes that result to a subset of the mutated molecules is shown in Table 3.

TABLE 3

| scFv selected from Naive Library | Mutation A.A (position) | Affinity μM (off rate) |
| --- | --- | --- |
| A9 | wt | 48 |
| A9.5 | S–V (98) | 15 |
| A9.13 | G–D (63) | 24 |
| | V–S (64) | 0.06 |
| E3 | wt | 18 |
| E3.1 | S–Q (82) | 9 |
| E3.2 | S–T (83) | 2 |
| C12 | wt | 11 |
| C12.1 | G–Q (48) | 5 |
| C12.2 | L–G (15) | 1 |

EXAMPLE 7

Expression of the antibody-fragment coding regions in *D. discoideum* is from the vector pAV1 which has has been constructed from the parent vector p569 (a gift from W. Nellen, Max-Planck Institute, Munich, Germany) and the $V_H$ coding region of the NC41$V_H$ as described below. The vector p569 is shown in FIG. 13; this is one of a family of vectors that are *E. coli/D. discoideum* shuttle vectors using the α-L fucosidase promoter and signal sequence for the secretion of the expressed "ligand binding peptide" to the cell surface. Table 4 shows the results from the immmodotblot of the expression of the Influenza NC41 $V_H$FLAG detected by the antiFLAG antibody (M2).

The $V_H$ coding sequence of the monoclonal antibody NC41 was amplified by Polymerase Chain Reaction using the oligonucleotide sequences:

N849(SEQ ID NO:5)

5'  CCTTGCCTGCAGGTCGACCTATGGACAGGTGCAGCTGCAGCAG  3'

N863

5'  TTACCATGGTTACTTGACCTTAATCAGCAGGACAAATGAAATAAATTTATCATCAT

CATCTTTATAATC  5'

N849 contains sequence complementary to the N-terminus of the NC41$V_H$ coding region together with the α-L-fucosidase signal sequence and cleavage site, as well as SalI restriction site suitable for cloning into the expression vector p569.

N863 (SEQ ID NO: 6) contains sequence complementary to the FLAG coding sequence of the NC41$V_H$, together with a transmembrane hydrophobic sequence, an NcoI restriction site for cloning and a translation stop codon.

DNA of the vector pAV 569 (a gift from W. Nellen, Max-Planck Institute, Martinsreid, Germany) was digested with the restriction enzyme NcoI and SaiI, and the cut vector was purified by the standard techniques of agarose electrophoresis and phenol extraction.

The PCR amplified and restriction digested NC41$V_H$ FLAG was ligated into the vector and the mixture was transformed into *E. coli*. Recombinant colonies were selected on ampicillin-containing YT plates and recombinant plasmids were recovered, purified and identified using standard techniques. The recombinant plasmid is designated pAV1.

The recombinant plasmid pAV1 was transformed into vegetative cells of *D. discoideum* by the feeding method disclosed in GB-2159821, by Friendlender and Mella.

Recombinant *D. discoideum* were selected using the antibiotic G418 at 10 μg/ml on DMB medium. Recombinant *D. discoideum* amoebae were grown in 2 ml cultures of DMB medium containing 10 μg/ml G418. After growth for 48 hours at 22° C., dot blot analysis was performed on 100 μl aliquots of the culture supernatant, and-an anti-FLAG antibody was used to detect the presence of the NC10$V_H$ FLAG antibody fragment in the culture. The results are summarised in Table 4.

TABLE 4

EXPRESSION OF NC41$V_H$–FLAG IN *D. DISCOIDEUM*
Immunodetection Dot Blot with Anti-FLAG Antibody

| *D. discoideum* clone # | Detection by Antibody |
| --- | --- |
| Negative Control | – |
| Negative Control | – |
| Positive Control | +++ |
| 9C Recombinant *D. discoideum* | + |
| 9D Recombinant *D. discoideum* | – |
| 9E Recombinant *D. discoideum* | ++ |
| 9F Recombinant *D. discoideum* | – |
| 9G Recombinant *D. discoideum* | ++ |
| 8B Recombinant *D. discoideum* | +++ |
| 8C Recombinant *D. discoideum* | – |
| 8D Recombinant *D. discoideum* | +++ |
| 8E Recombinant *D. discoideum* | +++ |
| 8F Recombinant *D. discoideum* | – |
| 8G Recombinant *D. discoideum* | +++ |
| 7D Recombinant *D. discoideum* | + |

TABLE 4-continued

EXPRESSION OF NC41$V_H$–FLAG IN *D. DISCOIDEUM*
Immunodetection Dot Blot with Anti-FLAG Antibody

| *D. discoideum* clone # | Detection by Antibody |
| --- | --- |
| 7E Recombinant *D. discoideum* | – |
| 7F Recombinant *D. discoideum* | + |
| 7G Recombinant *D. discoideum* | – |

– = no reaction
+++ = strong reaction
+ = weak reaction

EXAMPLE 8

Construction of the recombinant vector containing the 1C3Fab for expression in *D. discoideum*. The structure of the parent vector is shown in FIG. 13 (p569),and was modified by removal of a BamHI/BglII fragment by restriction digestion and religation, leaving unique XbaI and SspI sites for the cloning of the antibody coding regions that were constructed by the polymerase chain reaction with the primers (SEQ ID NOS: 7–8):

5' CAGGTCGACTCTAGAGTATGGGAGGTGAGGCTTCTCGAG 3'

5' AAATTTATAATTATTTATCATCATCATCTTTATAATC 3' and the 1C3Fab coding region (see Sequence I.D. 6) as template. This Fab is a polyfunctional polypeptide as it combines binding activities (TBRs) for glycophorin; and antiFLAG and anti EEF antibodies. Restriction digestion of the PCR products was followed by standard purification, ligation and transformation protocols for construction in *E. coli*. Transformation of *D. discoideum* is effected by feeding transformed *E. coli* (see GB-2159821A) or by standard methods by those skilled in the art as published in the literature such as by calcium phosphate crystals (Nellen et al, Mol. Cell. Biol., 1984 4 2890–2898) or electroporation (Howard et al, 1988, 16 2613–2623) with selection on G418 (geneticin).

It will be clearly understood that the invention in its general aspects is not limited to the specific details referred to hereinabove.

Description: JLApelB Ly – 2 + Ly – 3 V domains linked Mscl-Sali with FLAG tail
From base: 1-
To base: 849-
Total bases: 849-

```
      M  K  Y    L  L  P  T    A  A  A    G  L  L    L  L  A  A    Q  P  A
  1 ATGAAATACC TATTGCCTAC GGCAGCCGCT GGATTGTTAT TACTCGCTGC CCAACCAGCG

M  A  K    P  Q  A  P    E  L  R    I  F  P    K  K  M  D    A  E  L
 61 ATGGCCAAGC CACAGGCACC CGAACTCCGA ATCTTTCCAA AGAAAATGGA CGCCGAACTT

G  Q  K    V  D  L  V    C  E  V    L  G  S    V  S  Q  G    C  S  W
121 GGTCAGAAGG TGGACCTGGT ATGTGAAGTG TTGGGGTCCG TTTCGCAAGG ATGCTCTTGG

L  F  Q    N  S  S  S    K  L  P    Q  P  T    F  V  V  Y    M  A  S
181 CTCTTCCAGA ACTCCAGCTC CAAACTCCCC CAGCCCACCT TCGTTGTCTA TATGGCTTCA

S  H  N    K  I  T  W    D  E  K    L  N  S    S  K  L  F    S  A  M
241 TCCCACAACA AGATAACGTG GGACGAGAAG CTGAATTCGT CGAAACTGTT TTCTGCCATG

R  D  T    N  N  K  Y    V  L  T    L  N  K    F  S  K  E    N  E  G
301 AGGGACACGA ATAATAAGTA CGTTCTCACC CTGAACAAGT TCAGCAAGGA AAACGAAGGC

Y  Y  F    C  S  V  I    S  N  S    V  M  Y    F  S  S  V    V  P  V
361 TACTATTTCT GCTCAGTCAT CAGCAACTCG GTGATGTACT TCAGTTCTGT CGTGCCAGTC

L  Q  G    G  G  G  S    G  G  G    G  S  G    G  G  G  S    L  I  Q
421 CTTCAGGGTG GCGGAGGCTC AGGCGGTGGT GGATCAGGTG GCGGCGGATC TCTCATTCAG

T  P  S    S  L  L  V    Q  T  N    H  T  A    K  M  S  C    E  V  K
481 ACCCCTTCGT CCCTGCTGGT TCAAACCAAC CATACGGCAA AGATGTCCTG TGAGGTTAAA

S  I  S    K  L  T  S    I  Y  W    L  R  E    R  Q  D  P    K  D  K
541 AGCATCTCTA AGTTAACAAG CATCTACTGG CTGCGGGAGC GCCAGGACCC CAAGGACAAG

Y  F  E    F  L  A  S    W  S  S    S  K  G    V  L  Y  G    E  S  V
601 TACTTTGAGT TCCTGGCCTC CTGGAGTTCT TCCAAAGGAG TTTTGTATGG TGAAAGTGTG

D  K  K    R  N  I  I    L  E  S    S  D  S    R  R  P  F    L  S  I
661 GACAAGAAAA GAAATATAAT TCTTGAGTCT TCAGACTCAA GACGGCCCTT TCTCAGTATC

M  N  V    K  P  E  D    S  D  F    Y  F  C    A  T  V  G    S  P  K
721 ATGAATGTGA AGCCAGAGGA CAGTGACTTC TACTTCTGCG CGACGGTTGG GAGCCCCAAG

M  V  F    G  T  G  T    K  L  T    V  V  D    Y  K  D  D    D  D  K
781 ATGGTCTTTG GGACAGGGAC GAAGCTGACT GTGGTTGATT ACAAGGACGA CGATGACAAG

*  S  T
841 TAGTCGACA    (SEQ ID NOS: 10 and 9, respectively)
```

Description: Human single chain CD8 in pPOW (pelB CD8a and CD8b V dom)
From base: 1
To base: 822
Total bases: 822

```
      M  K  Y    L  L  P  T    A  A  A    G  L  L    L  L  A  A    Q  P  A
  1 ATGAAATACC TATTGCCTAC GGCAGCCGCT GGATTGTTAT TACTCGCTGC CCAACCAGCG

M  A  S    Q  F  R  V    S  P  L    D  R  T    W  N  L  G    E  T  V
 61 ATGGCCAGCC AGTTCCGGGT GTCGCCGCTG GATCGGACCT GGAACCTGGG CGAGACAGTG

E  L  K    C  Q  V  L    L  S  N    P  T  S    G  C  S  W    L  F  Q
121 GAGCTGAAGT GCCAGGTGCT GCTGTCCAAC CCGACGTCGG GCTGCTCGTG GCTCTTCCAG

P  R  G    A  A  A  S    P  T  F    L  L  Y    L  S  Q  N    K  P  K
181 CCGCGCGGCG CCGCCGCCAG TCCCACCTTC CTCCTATACC TCTCCCAAAA CAAGCCCAAG
```

-continued

```
         A    A    E         G    L    D    T         Q    R    F         S    G    K         R    L    G    D         T    F    V
241 GCGGCCGAGG   GGCTGGACAC   CCAGCGGTTC   TCGGGCAAGA   GGTTGGGGGA   CACCTTCGTC

L    T    L         S    D    F    R         R    E    N         E    G    Y         Y    F    C    S         A    L    S
301 CTCACCCTGA   GCGACTTCCG   CCGAGAGAAC   GAGGGCTACT   ATTTCTGCTC   GGCCCTGAGC

N    S    I         M    Y    F    S         H    F    V         P    V    F         L    P    A    G         R    G
361 AACTCCATCA   TGTACTTCAG   CCACTTCGTG   CCGGTCTTCC   TGCCAGCGGG   CGGCCGCGGT

S    G    G         G    S    G         G    G    G         S    L    Q         T    P    A         Y    I    K
421 TCAGGTGGAG   GTGGATCCGG   AGGCGGTGGA   TCTCTCCAGC   AGACCCCTGC   ATACATAAAG

V    Q    T         N    K    M    V         M    L    S         C    E    A         K    I    S    L         S    N    M
481 GTGCAAACCA   ACAAGATGGT   GATGCTGTCC   TGCGAGGCTA   AAATCTCCCT   CAGTAACATG

R    I    Y         W    L    R    Q         R    Q    A         P    S    S         D    S    H    H         E    F    L
541 CGCATCTACT   GGCTGAGACA   GCGCCAGGCA   CCGAGCAGTG   ACAGTCACCA   CGAGTTCCTG

A    L    W         D    S    A    K         G    T    I         H    G    E         E    V    E    Q         E    K    I
601 GCCCTCTGGG   ATTCCGCAAA   AGGGACTATC   CACGGTGAAG   AGGTGGAACA   GGAGAAGATA

A    V    F         R    D    A    S         R    F    I         L    N    L         T    S    V    K         P    E    D
661 GCTGTGTTTC   GGGATGCAAG   CCGGTTCATT   CTCAATCTCA   CAAGCGTGAA   GCCGGAAGAC

S    G    I         Y    F    C    M         I    V    G         S    P    E         L    T    F    G         K    G    T
721 AGTGGCATCT   ACTTCTGCAT   GATCGTCGGG   AGCCCCGAGC   TGACCTTCGG   GAAGGGAACT

Q    L    S         V    V    D    Y         K    D    D         D    D    K         *
781 CAGCTGAGTG   TGGTTGATTA   CAAGGACGAC   GATGACAACT   AC   (SEQ ID NOS: 12 and 11, respectively)
```

Description: MHCI a3 H-2K domain in pPOW pelB Msc-EcoRI (no FLAG)
From base: 1
To base: 371
Total bases: 371

```
         M    K    Y         L    L    P    T         A    A    A         G    L    L         L    L    A    A         Q    P    A
  1 ATGAAATACC   TATTGCCTAC   GGCAGCCGCT   GGATTGTTAT   TACTCGCTGC   CCAACCAGCG

M    A    K         A    H    V    T         H    H    R         R    P    E         G    D    V    T         L    R    C
 61 ATGGCCAAgG   CCCATGTCAC   CCATCACCGC   AGACCTGAAG   GTGATGTCAC   CCTGAGGTGC

W    A    L         G    F    Y    P         A    D    I         T    L    T         W    Q    L    N         G    D    E
121 TGGGCCCTGG   GCTTCTACCC   TGCTGACATC   ACCCTGACCT   GGCAGTTGAA   TGGGGACGAG

L    T    Q         E    M    E    L         V    E    T         R    P    A         G    D    G    T         F    Q    K
181 CTGACCCAGG   AAATGGAGCT   TGTGGAGACC   AGGCCTGCAG   GGGATGGAAC   CTTCCAGAAG

W    A    S         V    V    V    P         L    G    K         E    Q    K         Y    T    C    H         V    E    H
241 TGGGCATCTG   TGGTGGTGCC   TCTTGGGAAG   GAGCAGAAGT   ACACATGCCA   TGTGGAACAT

E    G    L         P    E    P    L         T    L    R         W    G    K         E    E    P    P         S    S    T
301 GAGGGGCTGC   CTGAGCCCCT   CACCCTGAGA   TGGGGCAAGG   AGGAGCCTCC   TTCATCCACC

K    *    N
361 AAGTAGAATT   C   (SEQ ID NO:14 and 13, respectively)
```

Linkerless 1C3 as Constructed in pHFA.
From Hind III site pHFA to start of gene 3 sequence.

```
                                                                                                                M    K    Y
    1 aag   ctt   gca   tgc   aaa   ttc   tat   ttc   aag   gag   aca   gtc   ata   ATG   AAA   TAC L    L    P    T    A    A    A    G    L    L    L    A    A    Q    P
   49 CTA  TTG  CCT  ACG  GCA  GCC  GCT  GGA  TTG  TTA  TTA  CTC  GCG  GCC  CAG  CCC A    M    A    E    V    K    L    Q    E    S    G    G    P    V    Q
   97 GCC  ATG  GCC  GAG  GTG  AAG  CTG  CAG  GAG  TCT  GGA  GGT  GGC  CCG  GTA  CAA P    G    G    S    L    K    L    S    C    A    A    S    G    F    D    F
  145 CCT  GGA  GGA  TCC  CTG  AAA  CTC  TCC  TGT  GCA  GCC  TCA  GGA  TTC  GAT  TTT S    R    Y    W    M    N    W    V    R    R    A    P    G    K    G    L
  193 AGT  AGA  TAC  TGG  ATG  AAT  TGG  GTC  CGG  CGG  GCT  CCA  GGG  AAG  GGG  CTA E    W    I    G    E    I    N    Q    Q    S    S    T    I    N    Y    S
  241 GAG  TGG  ATT  GGA  GAA  ATT  AAT  CAA  CAA  AGC  AGT  ACG  ATA  AAC  TAT  TCG P    P    L    K    D    K    F    I    I    S    R    D    N    A    K    S
  289 CCA  CCT  CTG  AAG  GAT  AAA  TTC  ATC  ATC  TCC  AGA  GAC  AAC  GCC  AAA  AGT T    L    Y    L    Q    M    N    K    V    R    S    E    D    T    A    L
  337 ACG  CTG  TAC  CTG  CAA  ATG  AAC  AAA  GTG  AGA  TCT  GAG  GAC  ACA  GCC  CTT
```

```
        Y   Y   C   A   R   L   S   L   T   A   A   G   F   A   Y   W
385    TAT TAT TGT GCA AGA CTT TCT CTT ACT GCG GCA GGG TTT GCT TAC TGG

G   Q   G   T   L   V   T   V   A   S   D   I   V   M   S   Q
433    GGC CAA GGG ACT CTG GTC ACC GTC GCC TCC GAC ATC GTC ATG TCA CAG

S   P   S   S   L   A   V   S   V   G   E   K   V   T   M   S
481    TCT CCA TCC TCC CTG GCT GTG TCA GTA GGA GAG AAG GTC ACT ATG AGC

C   R   S   S   Q   S   L   F   N   S   R   T   R   K   N   Y
529    TGC AGA TCC AGT CAG AGT CTG TTC AAC AGT AGA ACC CGA AAG AAC TAC

L   T   W   Y   Q   Q   K   P   G   Q   S   P   K   P   L   I
577    TTG ACT TGG TAC CAG CAG AAA CCA GGG CAG TCT CCT AAA CCG CTG ATC

Y   W   A   S   T   R   E   S   G   V   P   D   R   F   T   G
625    TAC TGG GCA TCC ACT AGG GAA TCT GGG GTC CCT GAT CGC TTC ACA GGC

S   G   S   G   T   D   F   T   L   T   I   S   S   V   Q   A
673    AGT GGA TCT GGG ACA GAT TTC ACT CTC ACC ATC AGC AGT GTG CAG GCT

E   D   L   A   D   Y   Y   C   K   Q   S   Y   N   L   R   T
721    GAA GAC CTG GCA GAT TAT TAC TGC AAG CAA TCT TAT AAT CTT CGG ACG

F   G   G   T   K   L   E   I   N   R   A   A   A   D   Y
769    TTC GGT GGA GGC ACC AAG CTG GAA ATT AAT CGG GCG GCC GCA GAT TAT

K   D   D   D   D   K   *   A   A   *   T   V   E   S   C   L
817    AAA GAT GAT GAT GAT AAA TAG GCC GCA TAG ACT GTT GAA AGT TGT TTA

A   K
865    GCA AAA . . . . . . . .   (SEQ ID NOS: /6 and 15, respectively)
```

```
                       pelB       signal     sequence
       M   K   Y   L   L   P   T   A   A   A   G   L   L   L   L   A   A   Q   P   A
       ATGAAATACCTATTGCCTACGGCAGCCGCTGGATTGTTATTACTCGCTGCCCAACCAGCG H1       Pst1                           H10
       M   A   Q   V   Q   L   Q   Q   S   G   A   E   L   V   K   P   G   A   S   V
       ATGGCGCAGGTGCAGCTGCAGCAGTCTGGGGCTGAACTGGTGAAGCCTGGGGCCTCAGTG H20                                  ┌────── H30 ──────┐
       R   M   S   C   K   A   S  │G   Y   T   F   T   N   Y│  N   M   Y   W   V   K
       AGGATGTCCTGCAAGGCTTCTGGCTACACATTTACCAATTACAACATGTACTGGGTAAAA H40                              H50              ┌─H52A─┐
       Q   S   P   G   Q   G   L   E   W   I   G   I   F   Y │P   G   N   G│ D   T
       CAGTCACCTGGACAGGGCCTGGAGTGGATTGGAATTTTTTATCCAGGAAATGGTGATACT H60                               H70
       S   Y   N   Q   K   F   K   D   K   A   T   L   T   A   D   K   S   S   N   T
       TCCTACAATCAGAAGTTCAAAGACAAGGCCACATTGACTGCTGACAAATCCTCCAACACA H80        H82A    H82C                       H90
       A   Y   M   Q   L   S   S   L   T   S   E   D   S   A   V   Y   Y   C   A   R
       GCCTACATGCAGCTCAGCAGCCTGACATCTGAGGACTCTGCGGTCTATTACTGTGCAAGA ┌────── H100 ──────┐          ┌── H100E ──┐                   BstE2
       S │G   G   S   Y   R   Y   D   G   G   F   D│ Y   W   G   Q   G   T   T   V
       TCGGGGGGCTCCTATAGATACGACGGAGGCTTTGACTACTGGGGCCAAGGGACCACGGTC H110                             linker                              L1
       T   V   S   G   G   G   G   S   G   G   G   G   S   G   G   G   G   S   D   I
       ACCGTCTCCGGTGGTGGTGGTTCGGGTGGTGGTGGTTCGGGTGGTGGTGGTTCGGATATC Sacl                     L10                                  L20
       E   L   T   Q   T   T   S   S   L   S   A   S   L   G   D   R   V   T   I   S
       GAGCTCACACAGACTACATCCTCCCTGTCTGCCTCTCTGGGAGACAGAGTCACCATCAGT ┌────── L30 ──────┐                              L40
       C   R   A │S   Q   D   I   S   N   Y│ L   N   W   Y   Q   Q   N   P   D   G
       TGCAGGGCAAGTCAGGACATTAGTAATTATTTAAACTGGTATCAACAGAATCCAGATGGA ┌─L50─┐                             L60
       T   V   K   L   L   I   Y │Y   T   S│ N   L   H   S   E   V   P   S   R   F
       ACTGTTAAACTCCTGATCTACTACACATCAAATTTACACTCAGAAGTCCCATCACGGTTC L70                                   L80
       S   G   S   G   S   G   T   D   Y   S   L   T   I   S   N   L   E   Q   E   D
       AGTGGCAGTGGGTCTGGAACAGATTATTCTCTCACCATTAGCAACCTGGAACAAGAAGAT
```

-continued

```
                         L90                                              L100
 I   A   T   Y   F   C   Q   Q  |D   F   T   L   P   F|  T   F   G   G   T
ATTGCCACTTACTTTTGCCAACAGGATTTTACGCTTCCGTTCACGTTCGGAGGGGGGACC

XhoI                    FLAG                       EcoR1
  K   L   E   I   R   D   Y   K   D   D   D   K   *   *
AAGCTCGAGATAAGAGACTACAAAGACGATGACGATAAATAATAAGAATTC
```

(SEQ ID NOS:18 and 17, respectively)

Description: anti-glycophorin 1C3 Fab
From base: 1
To base: 1443
Total bases: 1443

```
   1 aaaaaagcGG CCCAGCCGGC CATGGCCGAG GTGAGGCTTC TCGAGTCTGG AGGTGGCCCG

61 GTACAACCTG GAGGATCCCT GAAACTCTCC TGTGCAGCCT CAGGATTCGA TTTTAGTAGA

121 TACTGGATGA ATTGGgtcCG GCGGGCTCCA GGGAAGGGGC TAGAGTGGAT TGGAGAAATT

181 AATCAACAAA GCAGTACGAT AAACTATTCG CCACCTCTGA AGGATAAATT CATCATCTCC

241 AGAGACAACG CCAAAAGTAC GCTGTACCTG CAAATGAACA AAGTGAGATC TGAGGACACA

301 GCCCTTTATT ATTGTGCAAG ACTTTCTCTT ACTGCGGCAG GGTTTGCTTA CTGGGGCCAA

361 GGGACTCTGG TCACTGTCTC TGCAGCCAAA ACGACACCCC CATCTGTCTA TCCACTGGCC

421 CCTGGATCTG CTGCCCAAAC TAACTCCATG GTGACCCTGG GATGCCTGGT CAAGGGCTAT

481 TTCCCTGAGC CAGTGACAGT GACCTGGAAC TCTGGATCCC TGTCCAGCGG TGTGCACACC

541 TTCCCAGCTG TCCTGCAGTC TGACCTCTAC ACTCTGAGCA GCTCAGTGAC TGTCCCCTCC

601 AGCACCTGGC CCAGCGAGAC CGTCACCTGC AACGTTGCCC ACCCGGCCAG CAGCACCAAG

661 GTGGACAAGA AAATTgaaga attttaatta aaacatggaa ataaaGTGAA ACAAAGCACT

721 ATTGCACTGG CACTCTTACC GTTACTGTTT ACCCCGGTAA CCAAAGCCGA CATCGTCATG

781 TCACAGTCTC CATCCTCCCT GGCTGTGTCA GTAGGAGAGA AGGTCACTAT GAGCTGCAGA

841 TCCAGTCAGA GTCTGTTCAA CAGTAGAACC CGAAAGAACT ACTTGACTTG GTACCAGCAG

901 AAACCAGGGC AGTCTCCTAA ACCGCTGATC TACTGGGCAT CCACTAGGGA ATCTGGGGTC

961 CCTGATCGCT TCACAGGCAG TGGATCTGGG ACAGATTTCA CTCTCACCAT CAGCAGTGTG

1021 CAGGCTGAAG ACCTGGCAGA TTATTACTGC AAGCAATCTT ATAATCTTCG GACGTTCGGT

1081 GGAGGCACCA AGCTGGAAAT TAAACGGGCT GATGCTGCAG TATCCATCTT cCCACCATCC

1141 AGTGAGCAGT TAACATCTGG ATCTGGAGGT GCCTCAGTCG TGTGCTTCTT GAACAACTTC

1201 TACCCCAAAG ACATCAATGT CAAGTGGAAG ATTGATGGCA GTGAACGACA AAATGGCGTC

1261 CTGAACAGTT GGACTGATCA GGACAGCAAA GACAGCACCT ACAGCATGAG CAGCACCCTC

1321 ACGTTGACCA AGGACGAGTA TGAACGACAT AACAGCTATA CCTGTGAGGC CACTCACAAG
```

1381 ACATCAACTT CACCCATTGT CAAGAGCTTC AACAGGggaG AGTGTgcggc cgcagattat 1441 aaa (SEQ ID NO:19)

---

We claim:

1. A fusion protein comprising an immunoglobulin-like $V_L$ domain linked to an immunoglobulin-like $V_H$ domain, wherein said $V_L$ chain and said $V_H$ chain (A) are directly linked or (B) are linked via a peptide linker that consists of a chain of up to 10 amino acids.

2. A fusion protein according to claim 1, wherein said peptide linker consists of a chain of up to 10 amino acids.

3. A fusion protein according to claim 1, wherein said $V_H$ chain and said $V_L$ chain are directly linked.

4. A fusion protein according to claim 2, wherein said peptide linker consists of 5 or 10 amino acids.

5. A fusion protein according to claim 4, wherein said peptide linker consists of $Gly_4Ser$ or $(Gly_4Ser)_2$.

6. A fusion protein according to claim 2, wherein said peptide linker connects the C-terminus of the $V_H$ domain to the N-terminus of the $V_L$ domain.

7. A fusion protein according to claim 2, wherein said peptide linker connects the C-terminus of the $V_L$ domain to the N-terminus of the $V_H$ domain.

8. A fusion protein according to claim 3, wherein up to 13 amino acids of the $V_L$ domain at the junction of said $V_L$ and said $V_H$ domains are deleted.

9. A fusion protein according to claim 1, wherein said $V_H$ and said $V_L$ domains have different binding specificities.

10. A composition consisting essentially of dimeric or multimeric target binding polypeptides, wherein said dimeric or multimeric target binding polypeptides are formed by non-covalent association of monomeric units, wherein (i) each of said monomeric units comprises a fusion protein comprising an immunoglobulin-like $V_L$ domain covalently linked to an immunoglobulin-like $V_H$ domain and (ii) said $V_L$ chain and said $V_H$ chain are directly linked, or (iii) said $V_L$ chain and said $V_H$ chain are linked via a peptide linker.

11. A composition according to claim 10, wherein said composition consists essentially of dimeric units.

12. A composition according to claim 10, wherein said composition consists essentially of multimeric units.

13. A composition according to claim 11, wherein said $V_H$ and $V_L$ domains in said monomeric units have different binding specificities, whereby said dimeric units are bifunctional.

14. A composition according to claim 12, wherein said $V_H$ and $V_L$ domains in said monomeric units have different binding specificities, whereby said multimeric units are bifunctional or polyfunctional.

15. A polynucleotide molecule encoding a fusion protein according to claim 1.

16. A vector comprising a polynucleotide molecule according to claim 15.

17. A host cell transformed with a vector according to claim 16.

18. A method of producing a fusion protein, comprising culturing a host cell according to claim 17 and then isolating said fusion protein.

19. A pharmaceutical composition, comprising a fusion protein according to claim 1, together with a pharmaceutically-acceptable carrier.

20. A diagnostic reagent comprising a fusion protein according to claim 1, together with a diluent.

* * * * *